(12) United States Patent
Seki et al.

(10) Patent No.: US 8,610,904 B2
(45) Date of Patent: Dec. 17, 2013

(54) APPARATUS AND METHOD FOR INSPECTING A TAMPON

(75) Inventors: Shinobu Seki, Kagawa (JP); Hideki Onishi, Kagawa (JP); Masashi Hosokawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 111 days.

(21) Appl. No.: 13/129,882

(22) PCT Filed: Nov. 17, 2009

(86) PCT No.: PCT/JP2009/069495
§ 371 (c)(1),
(2), (4) Date: Jul. 28, 2011

(87) PCT Pub. No.: WO2010/058772
PCT Pub. Date: May 27, 2010

(65) Prior Publication Data
US 2011/0273727 A1    Nov. 10, 2011

(30) Foreign Application Priority Data
Nov. 21, 2008   (JP) ................................ 2008-298435

(51) Int. Cl.
*G01B 11/06*   (2006.01)
(52) U.S. Cl.
USPC ......................................... 356/634; 356/429

(58) Field of Classification Search
USPC .................... 356/238.1–238.3, 634
See application file for complete search history.

(56) References Cited

U.S. PATENT DOCUMENTS 3,863,636  A  *  2/1975  Johnson ........................ 604/358

FOREIGN PATENT DOCUMENTS

| JP | 06-273102 A | 9/1994 |
| JP | 10129935 | 5/1998 |
| JP | 2000-42031 A | 2/2000 |
| JP | 2006-271919 A | 10/2006 |

OTHER PUBLICATIONS

Extended European Search Report for Application No. 09827553.0 mailed Apr. 10, 2012.
ISR for PCT/JP2009/069495 mailed Feb. 16, 2010.

* cited by examiner

*Primary Examiner* — Tara S Pajoohi Gomez
(74) *Attorney, Agent, or Firm* — Lowe Hauptman & Ham, LLP

(57) ABSTRACT

An inspecting apparatus inspects a tampon that includes a tampon main body that has a cord and an applicator that is cylindrical and that accommodates the tampon main body in such a manner that the cord is exposed from a rear end of the applicator. The inspecting apparatus includes a suction mechanism that extends the cord along a longitudinal direction of the tampon by sucking air, and a cord-length inspecting mechanism that inspects a length of the cord while the suction mechanism is sucking the air.

6 Claims, 11 Drawing Sheets

LEADING END ←———→ REAR END

LEADING END ←———→ REAR END

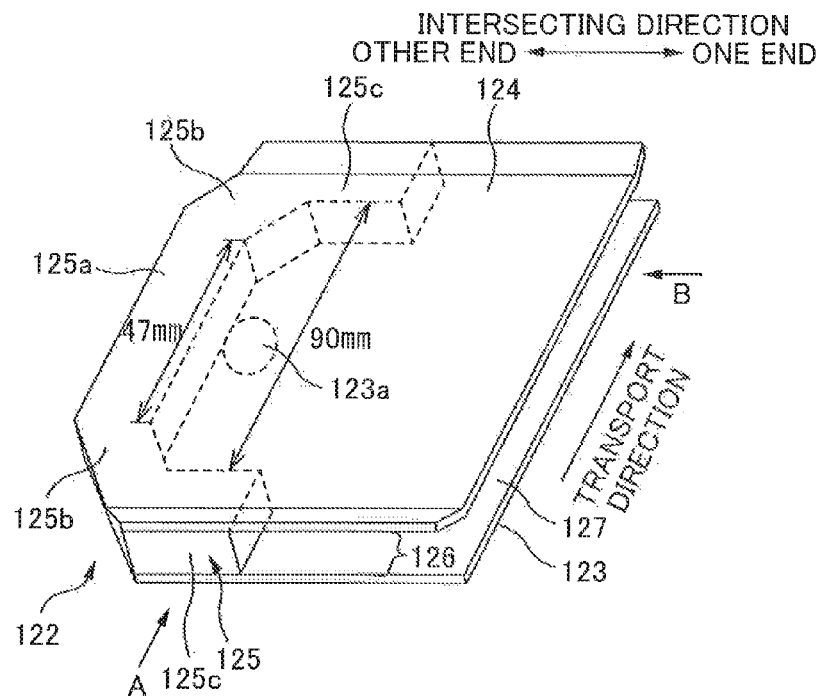
FIG. 12A
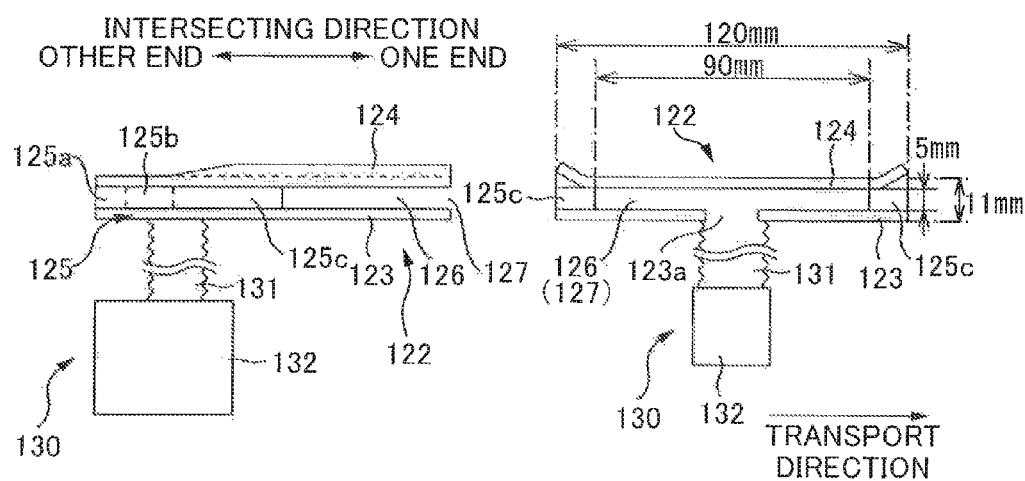
FIG. 12B
FIG. 12C

APPARATUS AND METHOD FOR INSPECTING A TAMPON

RELATED APPLICATIONS

The present application is National Phase of PCT/JP2009/069,495 filed Nov. 17, 2009, and claims priority from, Japanese Application Number JP2008-298,435, filed Nov. 21, 2008.

TECHNICAL FIELD

The present invention relates to an apparatus and method for inspecting a tampon. More particularly, the present invention relates to an apparatus and method for performing, on a tampon having a tampon main body that has a cord and an applicator that is cylindrical and that accommodates the tampon main body in such a manner that the cord is exposed from a rear end, an inspection of a length of the cord.

BACKGROUND ART

Tampons are widely known as a sanitary product. Some tampons have a tampon main body that has a cord and an applicator that is cylindrical and that accommodates the tampon main body in such a manner that the cord is exposed from a rear end. The cord is provided for pulling a tampon main body, which has been inserted in a vagina, out of the vagina.

The cord should be provided in a state where it has a normal length. Therefore, an inspection of a length of a cord may be performed on a tampon having the above structure (for example, Patent Literature 1).

CITATION LIST

Patent Literature

Patent Literature 1: JP-A-2000-42031

SUMMARY OF INVENTION

Technical Problem

It is obvious that a length of a cord needs to be inspected accurately. However, for example, if the cord swings or is slack due to floppiness, it will be difficult to inspect the length of the cord accurately.

The present invention has been made in view of such a disadvantage and the object of the present invention is to accurately perform, on a tampon having a tampon main body that has a cord and an applicator that is cylindrical and that accommodates the tampon main body in such a manner that the cord is exposed from a rear end, an inspection, of a length of the cord,

Solution to Problem in order to achieve the above-mentioned object, the main aspect of the present invention is:

an inspecting apparatus for inspecting a tampon, the tampon including a tampon main body that has a cord and an applicator that is cylindrical and that accommodates the tampon main body in such a manner that the cord is exposed from a rear end thereof, the inspecting apparatus comprising:

a suction mechanism that extends the cord along a longitudinal direction of the tampon by sucking air; and a cord-length inspecting mechanism that inspects a length of the cord while the suction mechanism is sucking the air.

Other features of the present invention will become apparent from descriptions of this specification and of accompanying drawings.

Advantageous Effects of Invention

According to an aspect of the invention, it is possible to accurately perform, on a tampon having a tampon main body that has a cord, arid an applicator that is cylindrical and that accommodates the tampon, main body in such a manner that the cord is exposed from a rear end, an inspection of a length of the cord.

BRIEF DESCRIPTION OF DRAWINGS

FIGS. 12A to 12C are schematic diagram of a casing 122.

MODE FOR CARRYING OUT THE INVENTION

Figure 1:
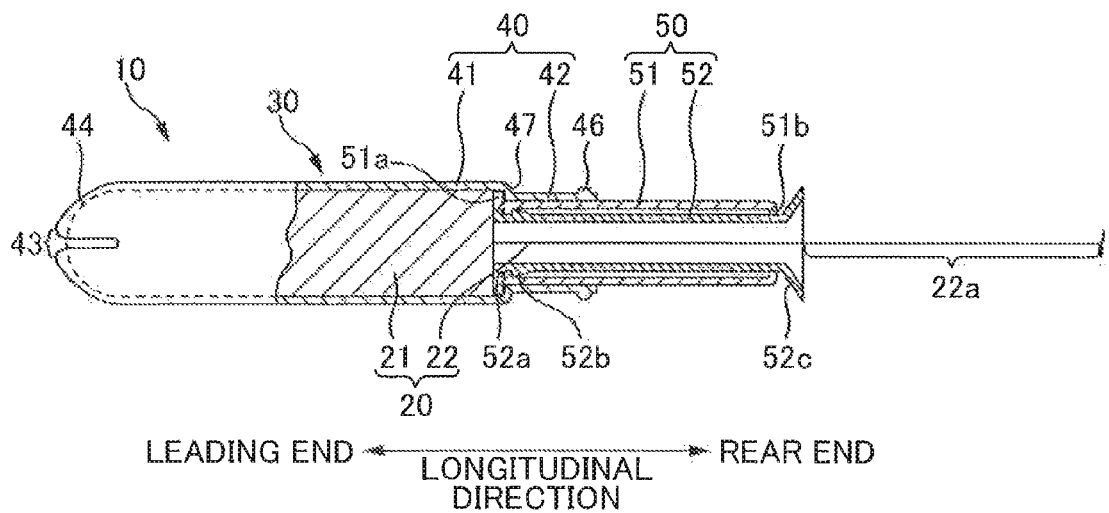
FIG. 1 is a cross-sectional view of elements of a tampon 10 (in a first state).

At least the following matters are disclosed in the present specification and accompanying drawings.

First, an inspecting apparatus for inspecting a tampon is provided in which, the tampon including a tampon main body that has a cord and an applicator that is cylindrical and that accommodates the tampon main body in such a manner that the cord is exposed from a rear end thereof, the inspecting apparatus including:

a suction mechanism that extends the cord along a longitudinal direction of the tampon by sucking air; and a cord-length inspecting mechanism that inspects a length of the cord while the suction mechanism is sucking the air.

With such an apparatus for inspecting a tampon, since the length of the cord is inspected in a state where the cord is extended along the longitudinal direction of the tampon, the length of the cord is accurately inspected.

Further, in the above-mentioned inspecting apparatus, the inspecting apparatus may further include:

a transport mechanism that transports the tampon in a transport direction that intersects with the longitudinal direction of the tampon, the cord-length inspecting mechanism includes:

a casing having a pair of walls, said wails opposing each other and lying along the transport direction; and a sensor that inspects the length of the cord, in a gap formed between the walls, the transport mechanism transports the tampon in such a manner that an exposing portion of the cord that is exposed from the rear end of the applicator passes through the gap along the transport direction, the suction mechanism extends the cord along the longitudinal direction of the tampon by sucking the air inside the casing while the exposing portion is passing through the gap, and the cord-length inspecting mechanism inspects the length of the cord by the sensor while the suction mechanism is slicking the air.

With such an apparatus for inspecting a tampon, the length of the cord, can be inspected in a state where the cord is straightened with a simple structure.

Further, in the above-mentioned inspecting apparatus, the casing may include:

the pair of walls;

an opening that is formed by opening the gap at one end side in an intersecting direction, said intersecting direction intersecting with the transport direction;

another wail that closes the gap at a side opposite to the opening in the intersecting direction; and a hole that is formed in either of the walls and one other wall, wherein the transport mechanism may transports the tampon in the transport direction with the longitudinal direction of the tampon lying along the intersecting direction and the tampon being situated on the opening side in the intersecting direction, a position at which the length of the cord is inspected by the sensor may be situated at a central part of the gap in the transport direction, the hole may be situated on the other wail side from the sensor in the intersecting direction, and the suction mechanism may suck the air inside the casing through the hole.

With such an apparatus for inspecting a tampon, the cord can be extended straight: when the exposing part of the cord passes through a central part of the gap in the transport direction. Then, since a position at which the length of the cord is inspected by the sensor is situated at the central part of the gap in the transport direction, the length of the cord can be inspected in a state where the cord is extended straight.

Further, in the above-mentioned inspecting apparatus, the cord-length inspecting mechanism may include a first optical sensor and a second optical sensor, the first optical sensor and the second optical sensor may be situated at mutually different positions in the intersecting direction, and the transport mechanism may transport the tampon in such a manner that, in a case where the length of the cord extended along the longitudinal direction of the tampon is normal, the rear end. of the cord passes between the first optical sensor and the second optical sensor in the intersecting direction.

With such an apparatus for inspecting a tampon, in a case where the length of the cord is shorter (or longer) than a normal length, a defect of the length of the cord can be positively detected.

Further, the above-mentioned inspecting apparatus, the inspecting apparatus may further include:

a pull-out mechanism that pulls out a portion that is to be the exposing portion from the rear end of the applicator, the pull-out mechanism may be provided upstream of the cord-length inspecting mechanism in the transport direction and pulls out the portion that is to be the exposing portion by sucking the air.

With such an apparatus for inspecting a tampon, when a portion of the cord that is supposed to be an exposing portion is not properly exposed from a rear end of the applicator such as by being buried in the applicator, such a portion can be pulled out. Thus, an inspection of the length of the cord can be performed with the exposing part being properly exposed.

Further, in the above-mentioned inspecting apparatus, the pull-out mechanism may include a suction pipe that extends along the intersecting direction.

a pair of cut-away portions opposing each other in the transport direction may be formed at a leading end part of the suction pipe, the transport mechanism may transport the tampon in such a manner that the rear end of the applicator passes through both of the pair of cut-away portions, and the pall-out mechanism may pull out the portion that is to be the exposing portion by sucking the air inside the suction pipe when the rear end of the applicator is situated between the cut-away parts in the transport direction.

With such an apparatus for inspecting a tampon, when a portion of the cord that is to be the exposing portion is not properly exposed from the rear end of the applicator, such a portion can be properly pulled out from the rear end of the applicator.

Further, in the above-mentioned inspecting apparatus, the inspecting apparatus may further include;

a contacting member that contacts the exposing portion, the contacting member may be provided upstream of the pull-out mechanism in the transport direction, and said, transport mechanism may transport the tampon in such a manner that the exposing portion contacts the contacting member and is caught by the contacting member.

With such an apparatus for inspecting a tampon, while the pull-out mechanism is performing a pull-out operation, the cord of the tampon that is positioned upstream of the tampon that is subject to the pull-out operation can be prevented from being sucked towards the pull-out mechanism. As a result, the cords can be prevented from being tangled with each other in the pull-out mechanism.

Further, an inspecting method of inspecting a tampon is provided in which, the tampon including a tampon main body having a cord, and an applicator that is cylindrical and accommodates the tampon main body in such a manner that the cord is exposed, from, a rear end. The inspecting method may include;

extending the cord along a longitudinal direction of the tampon by sucking air by a suction mechanism; and inspecting a length of the cord while the suction mechanism is sucking the air.

With such a method of inspecting a tampon, the length of the cord can be accurately inspected.

— Structure of Tampon 10 —

Figure 2:
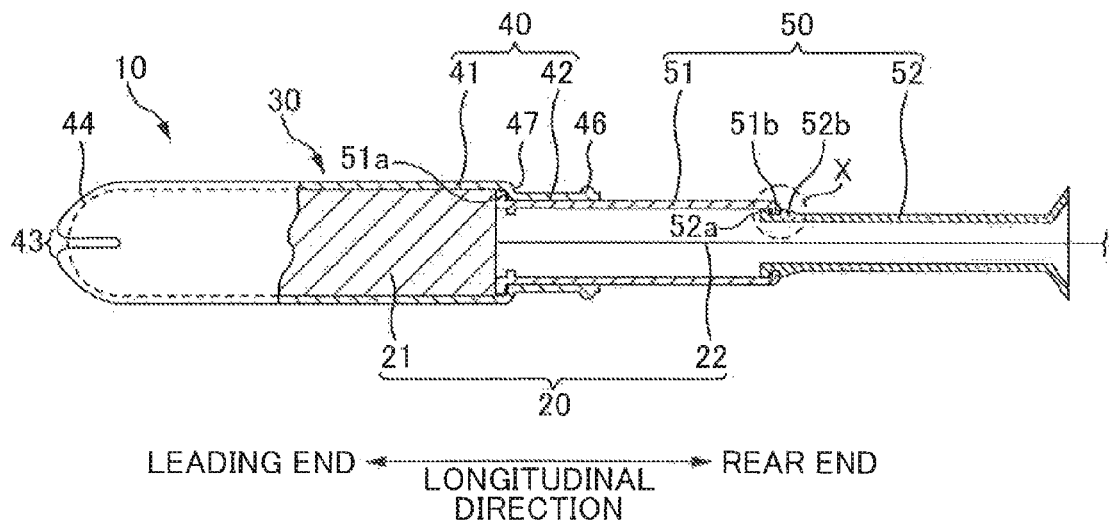
FIG. 2 is a cross-sections; view of elements of a tampon 10 (in a second, state).
Figure 3:
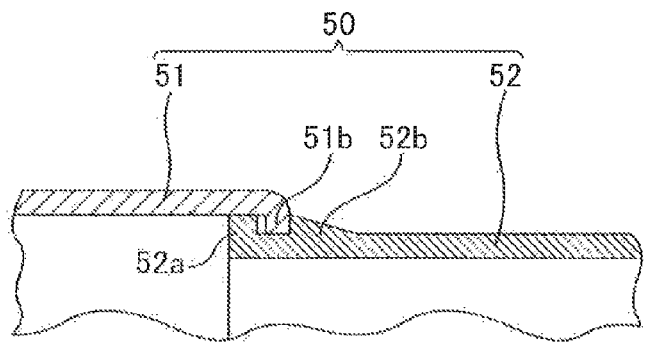
FIG. 3 is a diagram illustrating how a first inner cylinder 51 and a second inner cylinder 52 are connected.
Figure 4A:
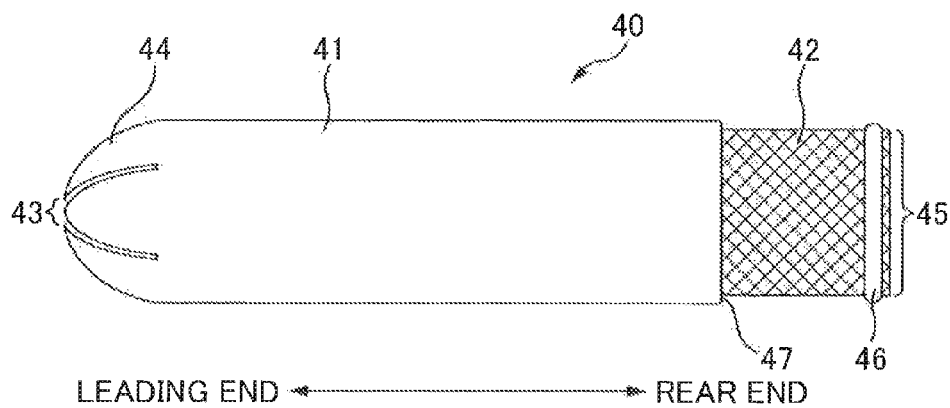
FIG. 4A and FIG. 4B are external views of an outer cylinder 40.
Figure 4B:
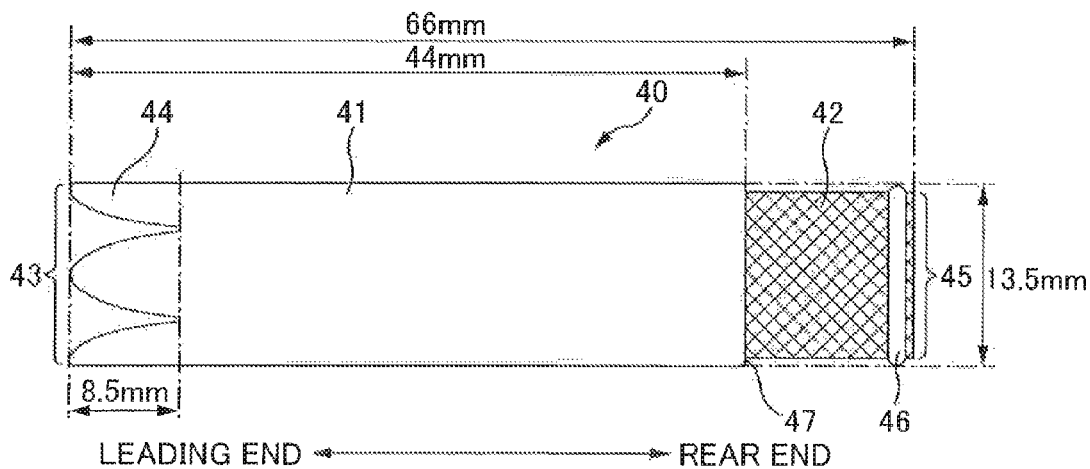
Figure 4C:
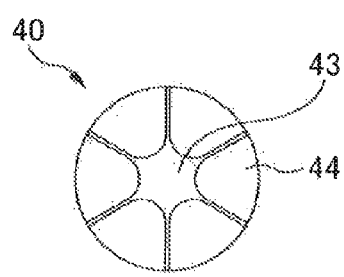
FIG. 4C is a diagram showing the outer cylinder 40 of FIG. 4A from the leading end side.
Figure 5:
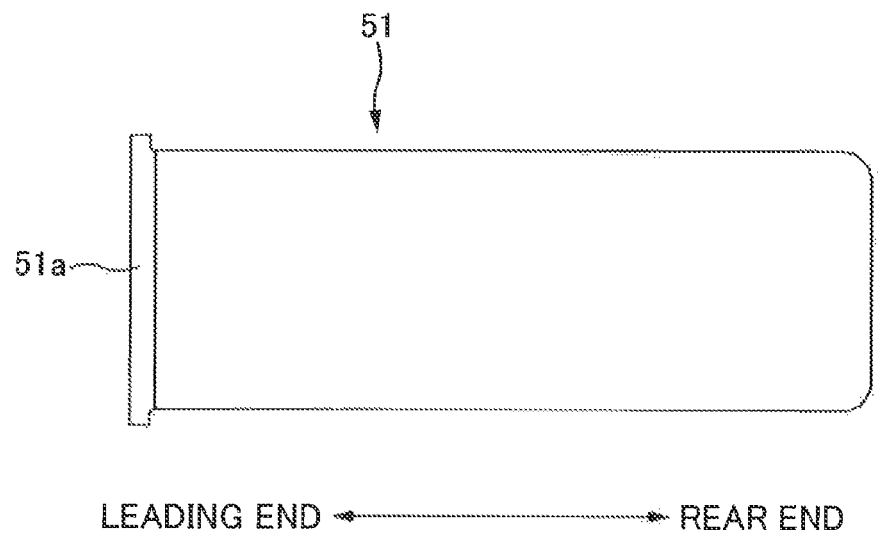
FIG. 5 is an external view of the first inner cylinder 51.
Figure 6:
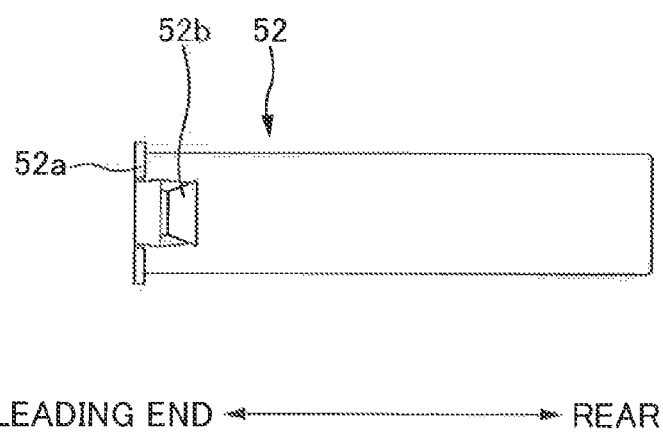
FIG. 6 is an external view of the second inner cylinder 52.

Structure of a tampon 10 of the present embodiment will be described with reference to FIGS. 1 to 6, FIGS. 1 and 2 are cross-sectional views illustrating components of a tampon 10. FIG. 1 shows the tampon 10 in a state where an inner cylinder 50 is contracted and. FIG. 2 shows the tampon 10 in a stare where the inner cylinder 50 is extended. FIG. 3 is a diagram illustrating how a first inner cylinder 51 and a second, inner cylinder 52 are connected and is an enlarged view of an area labeled "X" in FIG. 2. FIGS. 4A and 4B are external views of an outer cylinder 40. FIG. AC is a diagram showing the outer cylinder 40 of FIG. 4A from its leading end side. FIG. 5 is an external view of the first inner cylinder 51. FIG. 6 is an external view of the second inner cylinder 52. In the following description, along a longitudinal direction of the tampon 10, a side that is inserted into a vagina will be referred to as a leading end side and an opposite side will be referred to as a rear end side.

As shown in FIG. 1, the tampon 10 of the present embodiment is a sanitary product having a tampon main body 20 and an applicator 30. As shown in FIG. 1, the tampon main body 20 includes a cotton body 21 and a cord 22 sewn onto the cotton body 21. The cotton body 21 is an absorbent body that blocks a vaginal cavity and absorbs menstrual blood and the like. The cotton body 21 is formed by cutting a cotton strip 23 covered with non-woven fabric on both sides (see FIG. 8A), pressing the cotton strip 23 and then heat forming the cotton strip 23 into a substantially bullet like shape. The cord 22 extends from a rear end side of the cotton body 21 and. is held by a user when withdrawing the cotton body 21 from inside of the vaginal cavity to outside of the vaginal cavity. Also, as shown in FIG. 1, the cord 22 extends through the applicator 30 and is somewhat pulled out from a rear end of the applicator 30, In the following description, a portion of the cord 22 that is exposing from the rear end of the applicator 30 is referred to as an exposing portion 22a. An end of the cord 22 at a free end side is referred to as a rear end and an end on a fixed, end side (the cotton body 21 side) is referred to as a leading end of the cord 22.

The applicator 30 is a cylindrical member and accommodates the tampon main body 20 in a state where the cord 22 is exposed from the rear end thereof. The applicator 30 is also an aid device for facilitating the guiding of the tampon main body 20 (specifically, the cotton body 21) into the vaginal cavity. As shown in FIG. 1, the applicator 30 includes the outer cylinder 40 which is to be a part that accommodates the tampon main, body 20 and the inner cylinder 50 which pushes out the tampon main body 20 that has been accommodated in the outer cylinder 40.

The outer cylinder 40 is a cylindrical body made of a thermoplastic resin and has an appropriate flexibility. The outer cylinder 40 includes an major diameter part 41 provided at the leading end part and a minor diameter part 42 provided at the rear end part and that has an external diameter smaller than that of the major diameter part 41. The major diameter part 41 has an internal diameter that is slightly greater than the external diameter of the tampon main body 20, The tampon main body 20 is accommodated inside the major diameter part 41 of the outer cylinder 40. When using the tampon 10, the major diameter part 41 is inserted into the vaginal cavity with the tampon main body 20 being accommodated therein. Note that the tampon main body 20 is accommodated in the major diameter part 41 in such a manner that its outer peripheral surface is in contact with an inner peripheral surface of the major diameter part 41. The minor-diameter part 42 is a grip part held by a user when using the tampon 10, Note that the minor diameter part 42 is not necessarily provided on the outer cylinder 40.

As shown in Figs, 4A and 4B, the outer cylinder 40 includes a leading end opening 43 and a plurality of petaloid parts 44 (in the present embodiment, six petaloid parts 44) surrounding the leading end opening 43. Each of the plurality of petaloid parts 44 is provided at the leading end. part of the outer cylinder 40 and, at the time the tampon 10 is shipped, it is inwardly bent in an arc in the radial direction of the outer cylinder 40 as shown in FIG. 4A. Therefore, at the time the outer cylinder 40 is inserted into the vaginal cavity, the leading end part of the outer cylinder 40 is substantially hemispherical as shown in FIGS. 1 and 2, and the leading end opening 43 is substantially in a closed state as shown in FIG. 4C. As for the outer cylinder 40 directly after injection molding, as shown in FIG. 4B, each of the plurality or petaloid parts 44 is open and the leading end opening 43 is in an open state.

Further, as shown in FIG. 4A, the outer cylinder 40 includes a rear end. opening 45 and an annular rib 46 provided slightly towards the leading end side than the rear end opening 45, Further, an annular stepped part 47 is formed between the major diameter part 41 and the minor diameter part 42.

The inner cylinder 50 is a cylindrical body inserted in the minor diameter part 42 of the outer cylinder 40. The inner cylinder 50 is situated, at a position at the rear end side than the tampon main body 20 accommodated in the outer cylinder 40, travels along a central axis of the outer cylinder 40, and pushes the tampon main body 20 from the rear towards the leading end side opening 43. Thereby, the tampon main body 20 pushes each of the plurality of petaloid parts 44 outwardly in the radial direction of the outer cylinder 40 (i.e., opens the leading-end opening 43), and is pushed out of the outer cylinder 40. In other words, the inner cylinder 50 is movable in the outer cylinder 40 and has a function of pushing the tampon main body 20 out of the outer cylinder 40 through the leading end opening 43.

It is to be noted that the inner cylinder 50 of the present embodiment has a telescopic structure in order to provide a shorter overall length of the tampon 10 to make it compact. In detail, when the inner cylinder 50 is retracted as shown in FIG. 1, the length of the inner cylinder 50 becomes shorter than the length of the outer cylinder 40 and becomes a length that is convenient for carrying. On the other hand, when the inner cylinder 50 extends as shown in. FIG. 2, the length of the inner cylinder 50 becomes a length that is sufficient to push the tampon main body 20 out of the outer cylinder 40. In the present, embodiment, in order to achieve the telescopic structure of the inner cylinder 50, the inner cylinder 50 has a two-tier structure. In detail, as shown in FIG. 1, the inner cylinder 50 of the present embodiment includes the first inner cylinder 51 and the second inner cylinder 52 that is slidably inserted into the first inner cylinder 51. The first inner cylinder 51 is a cylindrical body made of plastic. The first inner cylinder 51 has an external diameter that is slightly :smaller than an internal diameter of the minor diameter part 42 of the outer cylinder 40. As shown in FIG. 1, the first inner cylinder 51 is slidably inserted into the minor diameter part 42, As shown in FIG. 5, an annular flange part 51a is formed on an outer peripheral surface of the leading end part of the first inner cylinder 51, The flange part 51a has an external diameter that is slightly smaller than the major diameter part 41 of the outer cylinder 40 and engages an inner wail of the stepped part 47, to thereby prevent the inner cylinder 50 from failing off from, the rear end opening 45 of the outer cylinder 40. When the inner cylinder 50 pushes the tampon main body 20 out of the outer cylinder 40, the inner cylinder 50 moves in such a manner that the outer peripheral surface of the flange part 51a comes into contact with the inner peripheral surface of the major diameter part 41, Further, as shown in FIGS. 1 and 2, at the rear end. side on an inner peripheral surface of the first inner cylinder 51, an annular protrusion 51b protruding inwardly in the radial direction of the first inner cylinder 51 is provided.

The second inner cylinder 52 is a cylindrical body made of thermoplastic resin. The second inner cylinder 52 has an external diameter that is slightly smaller than an internal diameter of the first inner cylinder 51, The second inner cylinder 52 is, when the inner cylinder 50 is in a contracted state, inserted in the first inner cylinder 51 as shown in FIG. 1 and, when the inner cylinder 50 is in an extended state, connected to the rear end part of the first inner cylinder 51 at the leading end part of one second inner cylinder 52 as shown in FIG. 2. As shown in FIG. 6, on the outer peripheral surface of the leading end part of the second inner cylinder 52, an arcuate flange part 52*a* and a protruded part. 52*b* provided at a position nearer to the rear end side than, the flange part 52*a* are formed. As shown in FIG. 3, a height of the protruded part 52*b* gradually lowers towards the rear end. Note that a space between the flange part 52*a* and the protruded part 52*b* of the second inner cylinder 52 is slightly greater than si thickness of the annular protrusion 51*b* of the first inner cylinder 51.

Then, as the second inner cylinder 52 is pulled towards the rear end side, the annular protrusion 51*b* of the first inner cylinder 51 will be at a position between the flange part 52*a* and the protruded part 52*b* of the second inner cylinder 52, In such a state, as shown in FIG. 3, the annular protrusion 51*b* engages the flange part 51*a* and the protruded part 52*b*, and thus the first inner cylinder 51 and the second inner cylinder 52 are connected.

Further, as shown in FIGS. 1 and 2, a flared part 52*c* is formed at the rear end part of the second inner cylinder 52. An external diameter of the flared part 52*c* is preferably at least greater than the internal, diameter of the first inner cylinder 51 and greater than or equal to the internal diameter of the minor diameter part 42 of the outer cylinder 40.

— Method of Manufacturing a Tampon 10 —

Figure 7:
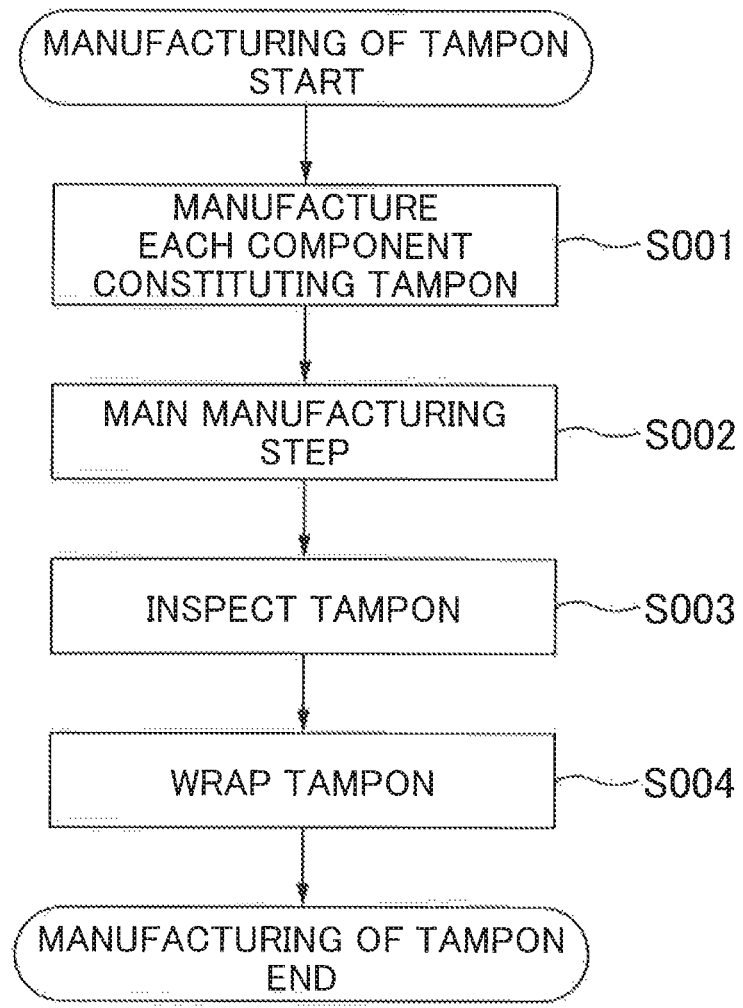
FIG. 7 is a flowchart showing a manufacturing flow of the tampon 10.

As shown in FIG. 7, a method of manufacturing the tampon 10 of the above-mentioned structure includes a step of manufacturing each component constituting the tampon 10 (hereinafter referred to as a component-manufacturing step S001), a step of manufacturing the tampon 10 by assembling each of the manufactured components into the tampon (hereinafter referred to as a main manufacturing step S002), a step of inspecting the manufactured tampon 10 (hereinafter referred to as an inspecting step S003) and a step of wrapping the tampon 10 (hereinafter referred to as a wrapping step S004). FIG. 7 is a flowchart showing a manufacturing flow of the tampon 10. Each of the above-mentioned steps will be described below.

<<Component-manufacturing Step S001>>

In the component-manufacturing step S001, the tampon main body 20, the outer cylinder 40 and the inner cylinder 50 (specifically, the first inner cylinder 51 and the second inner cylinder 52) which constitute the tampon 10 are manufactured, respectively.

Among the above-mentioned components, the outer cylinder 40, the first inner cylinder 51 and the second inner cylinder 52 are respectively manufactured by injection molding. It is to be noted that, the outer cylinder 40 is manufactured with each of the plurality of petaloid parts 44 being in an open, state (the outer cylinder 40 shown in FIG. 4B). The second inner cylinder 52 is manufactured without the flared part 52*c* being formed (the second inner cylinder 52 shown in FIG. 6).

Figure 8A:
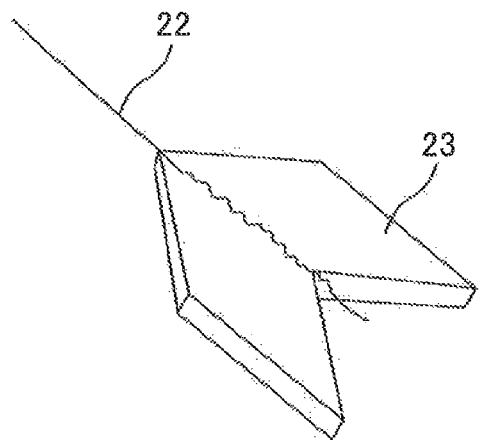
FIGS. 8A to 8C are explanatory diagrams showing a manufacturing procedure
of the tampon main body 20.
Figure 8B:
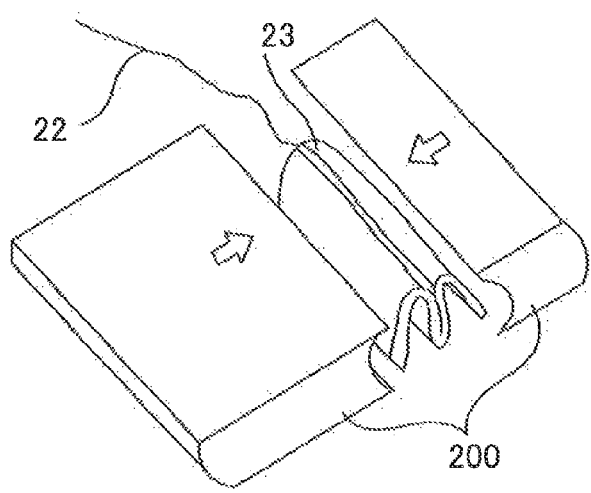
Figure 8C:
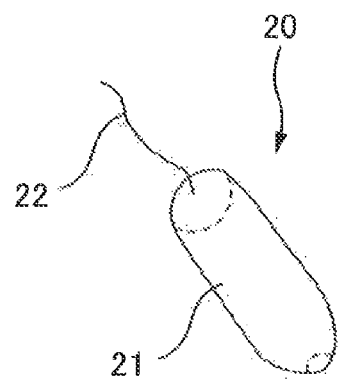

On the other hand, the tampon main body 20 is manufactured in accordance with a procedure shown in FIGS. 8A to 8C. FIGS. 8A to 8C are explanatory diagrams showing the procedure of manufacturing the tampon main body 20. In detail, first, a cotton strip 23 covered with non-woven fiber on both surfaces is cut in a fletching shape. Then, as shown in FIG. 8A, a cord 22 is sewn to the cut cotton strip 23, The cord 22 is continuously supplied and, after being sewn onto the cotton strip 23, the cord 22 is cut into a predetermined length (a length within a standard range) by a cutter (not shown). As shown in FIG. 5B, the cotton strip 23 with the cord 22 sewn thereon, is pressed into a cylindrical shape by a pressing machine 200. Thereafter, the cotton strip 23 is heat formed into a substantially bullet-like shape by a heat forming machine (not shown). With the procedure described above, the tampon main body 20 shown in FIG. 8C is manufactured.

<<Main Manufacturing Step S002>>

Referring to FIGS. 9A to 9D, the main manufacturing step S002 will be described. FIGS. 9A to 9D are transitional diagrams showing how the tampon 10 is manufactured.

The main manufacturing step S002 starts with supplying each of the components manufactured in the component-manufacturing step S001 to an assembly line. In the assembly line, each of the components is assembled into the tampon 10. First, the outer cylinder 40 formed by injection molding is supplied to the assembly line. Note that, as shown in FIG. 9A, the outer cylinder 40 at the time supplied to the assembly line is in a state where each of the plurality of petaloid parts 44 is open (i.e., the leading end opening 43 is in an open state).

Figure 9A:
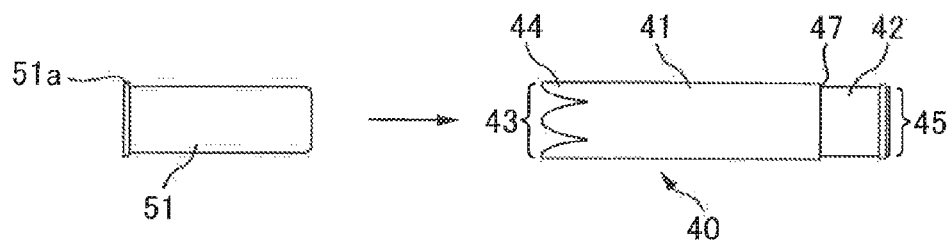
FIGS. 9A to 9D are transition diagram showing how the tampon 10 is manufactured.

Then, as shown in FIG. 9A, the first inner cylinder 51 formed by injection molding is inserted into the outer cylinder 40 through the leading end opening 43. The first inner cylinder 51 inserted into the outer cylinder 40 is in a state where its rear end part protrudes from the rear end opening 45 of the outer cylinder 40 and the flange part 51*a* engages with an inner wall surface of a stepped part 47 of the outer cylinder 40 (see FIG. 9B).

Figure 9B:
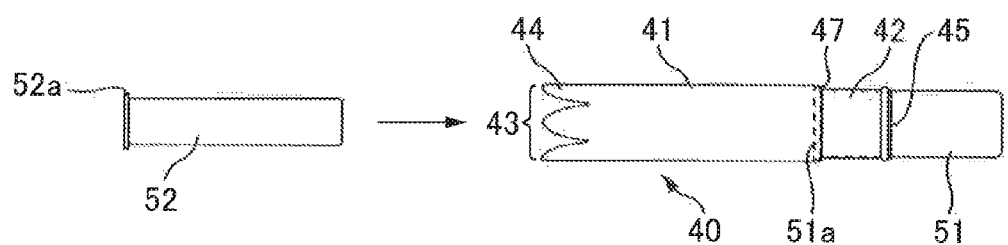

Then, as shown in FIG. 9B, the second inner cylinder 52 formed by injection molding is inserted into the outer cylinder 40 through the leading end opening 43. The second inner cylinder 52 inserted into the outer cylinder 40 is in a state where its rear end part is protruded from the opening on a rear end side of the first inner cylinder 51 and the flange part 52*a* engages with an inner peripheral surface of the first inner cylinder 51 (see FIG. 9C). After the second inner cylinder 52 has been inserted into the outer cylinder 40, the rear end part of the second inner cylinder 52 is heat formed to form a flared part 52*c*. With the steps described above, the assembling of the applicator 30 is completed.

Figure 9C:
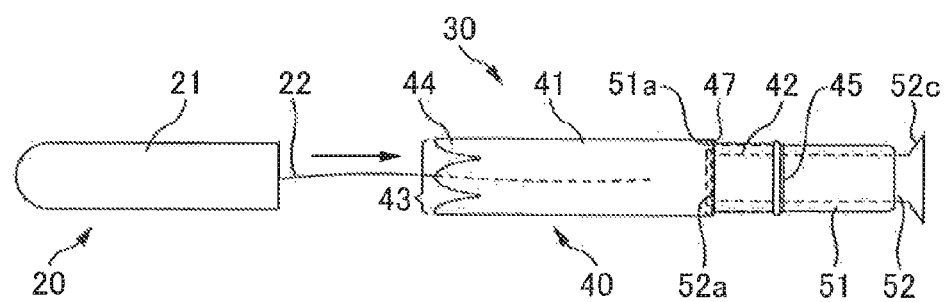

Thereafter, as shown in FIG. 9C, the tampon main body 20 manufactured in accordance with the above-described procedure is supplied to the assembly line and the tampon main body 20 is inserted into the outer cylinder 40 through the leading end opening 43. Here, as shown in FIG. 9C, the tampon main body 20 is inserted from a side where the cord 22 is provided. Thereby, the tampon main body 20 is accommodated in the outer cylinder 40 with a proper orientation. Then, as the tampon main body 20 is inserted into the outer cylinder 40, the cotton body 21 is accommodated in the major diameter part 41 of the outer cylinder 40 and the cord 22 somewhat extends out of the rear end of the applicator 30 (specifically, an opening on the rear end side of the second inner cylinder 52). In other words, the tampon main body 20 is accommodated in the applicator 30 and the exposing portion 22*a* of the cord 22 is exposed from the rear end of the applicator 30. With the steps described above, the assembly of the tampon 10 is completed.

Figure 9D:
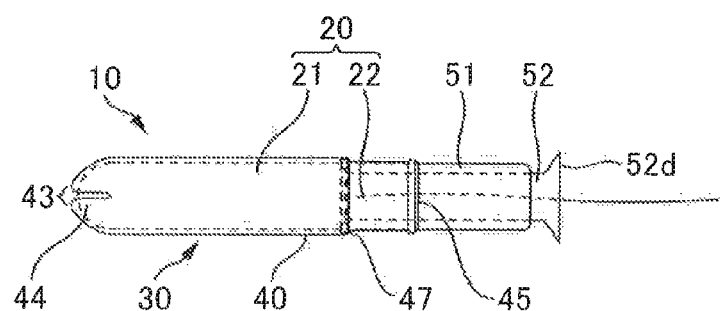

Then, as shown in FIG. 9D, after having assembled the tampon 10, a process of heat forming the leading end part of the outer cylinder 40 into a substantially hemispherical shape (hereinafter referred to as a leading end processing) is performed in which each of the plurality of petaloid parts 44 is bent in such, a manner that it is inclined inwardly in a radial direction of the outer cylinder 40. At the time the leading end process is terminated, the tampon 10 is finished and the main manufacturing step S002 is completed.

<<Inspecting Step S003>>

In an inspecting step S003, a step of inspecting a length of the cord 22 of the tampon ma in body 20 is performed on the tampon 10 manufactured in the main manufacturing step S002. This step is performed by an inspecting apparatus 100 described below and, in the present embodiment, performed on all the tampons 10. (I.e., a 100% inspection is performed). The tampons 10 are screened in accordance with the inspection results at the inspecting apparatus 100. In a case the length of the cord 22 is normal (specifically, the length within the standard range), the tampon 10 is transported to the wrapping step S004 at a later stage. On the other hand, the tarpon 10 having the cord 22 whose length is not normal is removed and collected.

It is to be noted that an inspecting method performed in the inspecting step S003 corresponds to the method, of inspecting the tampon 10 according to the present embodiment. In other words, the method of inspecting the tampon 10 according to the present embodiment includes a step of inspecting the length of the cord 22 provided on the tampon 10 (in detail, the cord 22 provided on the tampon main body 20 of the tampon 10). This step will be described in detail later.

<<Wrapping Step S004>>

In the wrapping step S004, the tampon 10 is inserted into a wrapping film having a bag-shape to wrap the tampon 10 individually. The wrapped tampons 10 are packed, in a box and thereafter shipped.

— Structure of Inspecting Apparatus 100 —

Figure 10:
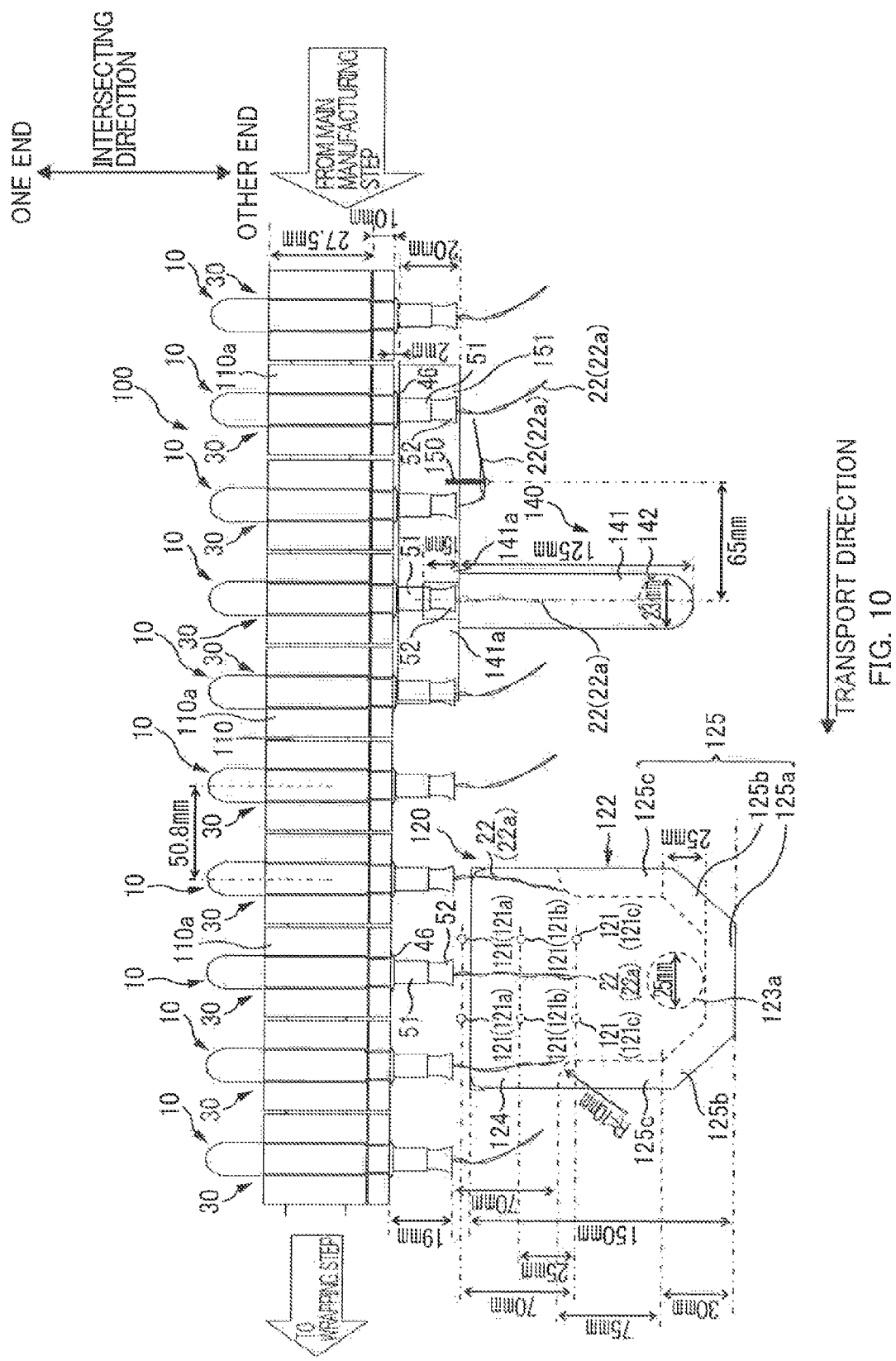
FIG. 10 is a schematic diagram illustrating an inspecting apparatus 100.

In explaining the step of inspecting the length, of the cord 22, the inspecting apparatus 100 implementing such step will be described with reference to FIG. 10. FIG. 10 is a schematic diagram illustrating the inspecting apparatus 100 and is an upper view of the inspecting apparatus 100. In FIG. 10, a transport direction of the tampon 10 and an interacting direction that intersects with the transport direction are shown by arrows.

The inspecting apparatus 100 of the present embodiment includes a transport mechanism 110 and a cord-length inspecting mechanism. 120 shown in FIG. 10, as well as a suction mechanism 130 (e.g., see FIG. 12B).

Figure 11:
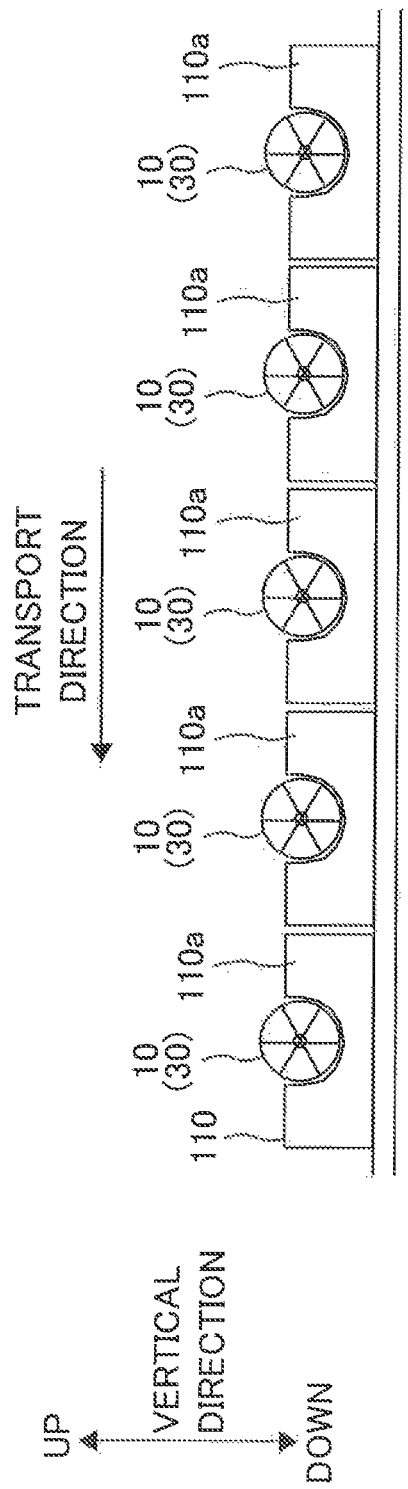
FIG. 11 is a side view of a transport mechanism 110.

The transport mechanism 110 transports the tampon 10 manufactured in the retain manufacturing step S002 in the transport direction that intersects with a longitudinal direction of the tampon 10. The transport direction in the present embodiment is a direction that is substantially perpendicular to the longitudinal direction or the tampon 10 and particularly a horizontal direction. As shown in FIG. 11, one transport mechanism 110 of the present embodiment includes a transport belt that extends along the transport direction and transports the tampon 10 together with a holder 110a, with tampon 10 being held by the holder 110a. FIG. 11 is a side view of the transport mechanism 110. The holder 110a is a substantially rectangular parallelepiped member that is fixed to the transport mechanism 110 and, as shown in FIG. 11, holds the tampon 10 by fitting the applicator 30 into a substantially hemicylindrical recess formed at a central part in the transport direction in the holder 110a.

The tampon 10 held by the holder 110a takes a posture in which its longitudinal direction lies along the intersecting direction (a transversely-situated posture). Here, the intersecting direction is a direction that intersects with the transport direction and, in the present embodiment, it is a direction that intersects with the transport direction in a horizontal plane. Then, the transport mechanism 110 transports the tampon 10 in the transport direction while maintaining the posture of the tampon 10 in the above-mentioned posture. In the following description, regarding the intersecting direction, a side where the leading end of the tampon 10 is situated as seen from a rear end of the tampon 10 that is being transported is referred, to as a one-end side and a side where the rear end of the tampon 10 is situated as seen from the leading end of the tampon 10 is referred to as an other-end side (see FIG. 10).

As shown in FIG. 10, the transport mechanism 110 sequentially transports the tampons 10 at a certain spacing in the transport direction (in the present embodiment, the spacing is approximately 50.8 mm) , During this, each tampon 10 travels while taking the same position in the intersecting direction. That is to say, each tampon 10 travels to a downstream side in the transport direction in such a manner that positions of the leading ends of the tampons 10 are situated at the same position in the intersecting direction.

To be more specific, a plurality of holders 110a are arranged in in a series along the transport direction and are transported in the transport direction with the positions of the holders 110a in the intersecting direction being the same. Each tampon 10 is held by the holder 110a in such a manner that a leading-end-side end surface of the annular rib 46 provided on. the outer cylinder 40 is in contact with an other-end surface of the holder 110a that is at the other end in the intersecting direction (see FIG. 10). Thus, each tampon 10 is transported in the transport, direction together with the holder 110a in such, a manner that, the leading end positions of the tampons 10 are the same among the tampons 10.

The cord-length inspecting mechanism 120 performs an inspection of the length of the cord 22 on each tampon 10, while each tampon 10 is being transported. As shown in FIG. 10, the cord-length inspecting mechanism 120 includes a sensor 121 and a casing 122.

The sensor 121 is provided for the cord-length inspecting mechanism 120 to inspect the length of the cord 22 and is provided on the other-end side in the intersecting direction as seen from the tampon 10 that, is being transported. The sensor 121 of the present embodiment is an optical sensor that irradiates light and detects the presence of the cord 22 on an optical path of the irradiate light when the irradiated light is interrupted.

In the present embodiment, three sensors 121 are provided that are aligned along the intersecting direction. The three sensors 121 are situated in such a manner that their positions are substantially the same in the transport direction and are mutually different in the intersecting direction, hereinafter, among the three sensors 121, the sensor 121 situated at the most one-end side in the intersecting direction (the sensor 121 situated at a position nearest to the tampon 10 that is being transported) is referred to as a one-end side sensor 121a, the sensor 121 situated at the most other-end side (she sensor 121 situated at a position furthest from the tampon 10 that is being transported) is referred to as an other-end side sensor 121c, and. the sensor 121 situated between the one-end side sensor 121a and the other-end side sensor 121c is referred to as a middle sensor 121b.

The one-end side sensor 121a is situated at a position offset from a reference position by approximately 19 mm on the other end side in the intersecting direction. Here, the reference position is a position which is taken as a reference by the cord-length inspecting mechanism 120 when inspecting the cord 22 of each tampon 10. The reference position in the present embodiment corresponds to a position of the other-end-surface of the holder 110a in the intersecting direction. As has been described above, in a state where the tampon 10 is held by the holder 110a, the leading-end-side end-surface of the annular rib 48 of the outer cylinder 40 of the tampon 10 is provided on the tampon 10 is in contact with the other-endsurface of the holder 110a in the intersecting direction. Thus, the reference position corresponds to the position of the leading-end-side end-surface of the annular rib 46 of the outer cylinder 40 of each tampon 10. It is to be noted that the reference position is not limited to the above-mentioned position and can be any another position (e.g., a position of the rear end of the applicator 30).

The one-end side sensor 121a detects the presence or absence of the cord 22 at a position that is slightly to the other-end side in the intersecting direction than the rear end of the applicator 30, when the rear end of the applicator 30 of the tampon 10 comes to the same position as a the one-end side sensor 121a in the transport direction. That is, the one-end side sensor 121a is a sensor 121 that detects whether the cord 22 of the tampon 10 is exposed from the rear end of the applicator 30 (i.e., presence or absence of the exposing part 22a) and is provided for inspecting whether the cotton body 21 to which the cord 22 is sewn, (i.e., the tampon main body 20) is accommodated in the applicator 30 and whether the cord 22 is sewn to the cotton body 21 in the applicator 30. Note that it is not necessary to provide the one-end side sensor 121a.

The middle sensor 121b is a sensor 121 that is situated on the other-end. side in the intersecting direction by approximately 45 mm from the one-end side sensor 121a and corresponds to a first optical sensor. The other-end side sensor 121c is a sensor 121 that is situated on the other-end side in the intersecting direction by approximately 70 mm from the one-end side sensor 121a and corresponds to a second optical sensor.

When the rear end of the applicator 30 of the tampon 10 comes to the same position as the one-end side sensor 121a in the transport direction, if the cord 22 provided on the tampon 10 has a normal length 8 (a length within, a standard range) and is also extending straight, the rear end of the cord 22 passes between the middle sensor 121b and the other-end side sensor 121c in the intersecting direction. That is to say, when the length of the cord. 22 that is extended straight along the longitudinal direction of the tampon 10 is normal, the above-mentioned transport, mechanism 110 transports the tampon 10 in such a manner that the rear end of the cord 22 passes between the middle sensor 121b and the other-end side sensor 121c in the intersecting direction.

As has been described above, among the sensors 121, the middle sensor 121b and the other-end side sensor 121c are the sensors 121 provided in the cord-length inspecting mechanism 120 for inspecting whether the cord 22 of each tampon 10 has a normal length. To be more specific, when the middle sensor 121b has detected the cord 22 and the other-end side sensor 121c has not detected the cord 22, the cord-length inspecting mechanism 120 determines that the length of the cord 22 is normal.

Further, in the present embodiment, sis shown in FIG. 10, each of the one-end side sensor 121a, the middle sensor 121b and the other-end side sensor 121c is provided one each at two pieces in the transport direction. Each of the two one-end side sensors 121a is situated at the same position in the intersecting direction. Similarly, each of the two middle sensors 121b and each of the two other-end side sensors 121c are situated at the same positions in the intersecting direction, respectively. As has been described above, in. the present, embodiment, two sets of combination of the one-end side sensor 121a, the middle sensor 121b and the other-end side sensor 121c are provided, Thus, the inspection accuracy of the cord-length inspecting mechanism 120 is improved. Note that, the number of sets of combination of the one-end side sensor 121a, the middle sensor 121b and the other-end side sensor 121c is not limited to two sets. For example, a single set of such combination or more than two sets of such combination may be provided.

The casing 122 is a frame body provided on the other-end side in the intersecting direction as seen, from the tampon 10 being transported, and includes, as shown in Figs, 12A to 12C, a lower wall 123, an upper wail 124 and a side wall 125, FIGS. 12A to 12C are diagrams schematically illustrating the casing 122. FIG. 12A is a perspective view of the casing 122. FIG. 12B is a front view of the casing 122 and is a diagram illustrating the casing 122 seen from a direction of an arrow A in FIG. 12A. FIG. 120 is a side view of the casing 122 and is a diagram illustrating the casing 122 seen from a direction of an arrow B in FIG. 12A.

The lower wall 123 and the upper wall 124 are an example of a pair of walls and are arranged in such a manner that they opposes each other in the vertical direction. Each of the lower wail 123 and the upper wall 124 is a fiat wail placed substantially horizontally and extends along the transport direction. Further, as shown in FIG. 12A, each of the lower wall 123 and the upper wail 124 has a substantially homebase shape when viewed in the vertical direction. Note that the shape of each of the lower wall 123 and the upper wall 124 is not limited to the shape of the present embodiment and may be, for example, substantially rectangular, substantially triangular or substantially semicircular when viewed from above.

Also, a gap 126 is formed between the lower wall 123 and the upper wall 124. In the present embodiment, the width (a size along the vertical direction) of the gap 126 is approximately 5 mm and the depth (a size along the transport direction) is approximately 120 mm (see FIG. 12C.

In the present embodiment, both end parts in the transport, direction of the upper wall 124 is bent upwards and away from the lower wall 123, That is, as shown in FIG. 12C, the upper wall 124 is substantially arcuate when viewed in the intersecting direction and a spacing of the gap 126 is somewhat greater at the both end parts in the transport direction than the spacing at the central part in the transport direction.

The side wall 125 is an example of another wall, and, as shown in FIGS. 12A and 12B, it is sandwiched between the lower wall 123 and the upper wall 124 and has a substantially U shape when viewed from above. In detail, the side wall 125 includes a central part 125a provided at the central part in. the transport direction, angled parts 125b provided adjacent to both end parts of the central part 125a, respectively, each of the angled parts 125b being angled in such a manner that it reaches toward, the the one-end side in the intersecting direction as it gets away from the central part 125a, and end parts 125c that are provided at both end parts in the transport direction of the side wall 125, respectively. and that lie along the intersecting direction. A one end in the intersecting direction of each of the end parts 125c is situated somewhat on the other-end side in the intersecting direction than one end in the intersecting direction of each of the lower wail 123 and the upper wall 124. Note that the position of the one end in the intersecting direction of the end part 125c is situated on the other-end side in the intersecting direction by approximately 89 mm from, the reference position (see FIG. 10).

As shown in FIG. 12, the side wall 125 closes the other-end part in the intersecting direction of the gap 126, On the other hand, the one end in the intersecting direction of the gap 126 is an open end. That is to say, the casing 122 includes an opening 127 that is formed in such a manner that the gap 126 is open at the one-end side in the intersecting direction. Also, the side wall 125 closes the gap 126 on the other side of the opening 127 in the intersecting direction.

The casing 122 has a hole 123a that penetrates through the lower wall 123 in a vertical direction. This hole 123a is a circular hole that, is formed in the central part in the transport direction of the lower wall 123 and that is situated somewhat to the one-end side than the other end in the intersecting direction of the lower wail 123 (specifically, slightly to the one-end side than the one-end surface in the intersecting direction of the central part 125a of the side wail 125. A duct 131, which is to be described later, is connected at a position where the hole 123a is formed in the lower wall 123, Note that the position at which the hole 123a is formed is not limited to the position described above and the hole 123a should be formed in either of the lower wall 123, the upper wall 124 and the side wall 125.

The casing 122 of the above-described structure is arranged in. such a manner that applicator 30 of the tampon 10 travels in the vicinity thereof. In detail, the transport mechanism 110 transports each of the tampons 10 in the transport direction, with the tampon 10 being situated on the opening 127 side in the intersecting direction, in such a manner that the rear end of the applicator 30 opposes the opening 127 (see FIG. 10).

Further, in the present embodiment, the casing 122 is arranged in such a manner that, when the tampon 10 is transported in the transport direction, the exposing portion 22a of she cord 22 provided on the tampon 10 passes through the gap 126 formed between the lower wall 122 and the upper wall 124. That is to say, the transport, mechanism 110 of the present embodiment transports the tampon 10 in such a manner that the exposing portion 22a passes through the gap 126 along the transport direction.

Also, the above-mentioned middle sensor 121b and the other-end side sensor 121c are accommodated in the casing 122, In detail, the middle sensor 121b and the other-end side sensor 121c are mounted on an inner wall surface of one of the lower wall 123 arid the upper wall 124. That is to say, the middle sensor 121b and the other-end side sensor 121c are the sensors 121 for inspecting, in the gap 126, the length of the cord. 22 that passes through the gap 126. Further, the position at which the length of the cord 22 is detected by each of the middle sensor 121b and the other-end side sensor 121c is situated inside the gap 126 and, in the present embodiment, situated at the central part in the transport direction of the gap 126. Also, the position at which the presence and absence of the exposing portion 22a of the cord 22 is detected by the other-end side sensor 121a is situated outside the gap 126 (on the one-end side than the opening 127 in the intersecting direction).

In the present embodiment, each of the sensors 121 is situated on the one-end side in the intersecting direction of the position at which the hole 123a is formed, (see FIG. 10). In other words, the hole 123a is situated on the side wall 125 side (the other end side) in the intersecting direction of each of the sensors 121 (specifically, the other-end side sensor 121c).

A suction mechanism 130 sucks air inside the casing 122 through the hole 123a (specifically, air inside the gap 126). The suction mechanism 130 includes a duct 131, and suction pump 132 as a suction source (see FIG. 12C). The duct 131 is an accordion-type duct provided between the suction, pump 132 and the hole 123a, and forms a wind path when the suction pump 132 sucks the air inside the casing 122. The suction pump 132 sucks the air at a predetermined suction pressure (in the present embodiment, approximately 0.7 kPa). Note that, in the present embodiment, an internal diameter of the duct 131 (in the present embodiment, approximately 34 mm) is slightly greater than a diameter of the hole 123a (in the present embodiment, approximately 25 mm).

With the suction mechanism 130 of a structure described above, a suction operation by the suction pump 132 is performed while the cord 22 (specifically, the exposing portion 22a of the cord 22) of each of the tampons 10 is passing through the gap 125. With such a suction operation, the cord 22 is extended straight along the longitudinal direction of the tampon 10, while passing through the central part in the transport direction of the gap 126. In the present embodiment, while the inspecting apparatus 100 is in operation, the suction pump 132 is continuously operating. However, it is not limited to such an embodiment, and, for example, the suction pump 132 may be operated (perform a suction operation) only during a period when the exposing portion 22a of the cord 22 is passing through the gap 126. Also, the position at which the suction mechanism 130 is situated may be any position as long as the suction operation is performed in a manner described above.

The cord-length inspecting mechanism 120 having the above-mentioned sensors 121 and the casing 122 inspects the length of the cord 22 of each of the tampons 10 with the above-described three sensors 121 while the suction mechanism 130 is sucking air. To be more specific, the cord-length inspecting mechanism 120 inspects the length of the cord 22 with the above-mentioned three sensors 121 when the exposing portion 22a of the cord 22 passes through the central part in the transport direction of the gap 126 (i.e., while the cord 22 is being extended along the longitudinal direction of the tampon 10). The inspection operation of the cord-length inspecting mechanism 120 will be described in detail later in the next section.

As shown in FIG. 10, in addition to the above-mentioned devices, the inspecting apparatus 100 of the present embodiment further includes a pull-out mechanism 140 and a contacting member 150. The pull-out mechanism 140 is a mechanism that forcedly pulls out the cord 22 (specifically, a portion that is supposed to be the exposing portion 22a) from the rear end of the applicator 30 when a portion of the cord 22 of the tampon 10 that is supposed to be the exposing portion 22a is buried inside the applicator 30 and is not properly exposed from the rear end of the applicator 30 due to twist and slack.

In the present embodiment, the pull-out mechanism 140 is provided upstream of the cord-length inspecting mechanism 120 in the transport direction. The pull-out mechanism 140 pulls out the cord 22 by performing a suction operation that sucks air from the rear end side of the applicator 30 of each of the tampons 10 (hereinafter referred to as a pre-suction operation). In order to perform such a pre-suction operation, the pull-out mechanism 140 includes a suction pipe 141 shown in FIG. 10 and a suction source.

The suction pipe 141 is, in the transport direction, situated upstream of the cord-length inspecting mechanism 120. The air inside the suction pipe 141 is sucked by the suction source of the pull-out mechanism 140. The suction pipe 141 extends along the intersecting direction. At the rear end part (an end part on the other-end side in the intersecting direction) of the suction pipe 141, a connection pipe 142 is connected that has a diameter different from that of the suction pipe 141. The suction, pipe 141 is connected to a suction inlet (not shown) of the above-mentioned suction source via the connection pipe 142.

Figure 13:
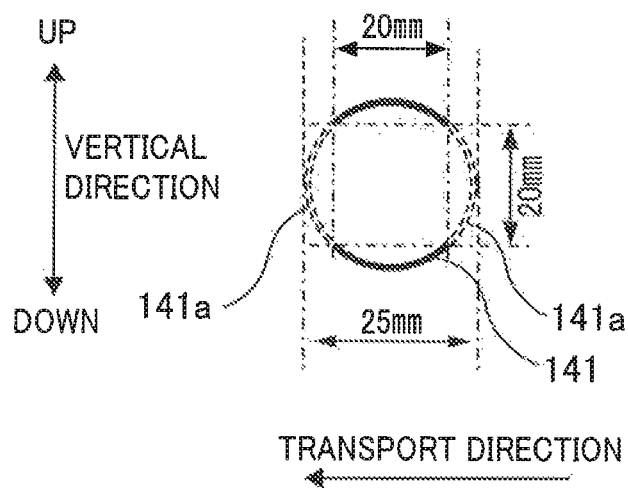
FIG. 13 is a diagram showing a leading end opening of a suction pipe 141.

Also, as shown in FIG. 13, on an outer peripheral surface of a leading end part (an end part on the one-end side in the intersecting direction) of the suction pipe 141, a pair of cutaway portions 141a is formed that opposes each other in the transport direction. FIG. 13 is a diagram showing a leading end side opening of the suction pipe 141. Each of the cutaway portions 141a has a height of approximately 20 mm in the vertical direction and a width of approximately 15 mm in the intersecting direction (see FIGS. 10 and 13). Note that the height of each of the cut-away portions 141a is greater than the external diameter of the rear end part of the applicator 30 (specifically, external diameters of the first inner cylinder 51 and the second inner cylinder 52).

Then, as shown in FIG. 10, the tampon 10 travels in the transport direction in such a manner that the rear end of the applicator 30 passes both of the pair of cut-away portions 141a. In other words, the transport mechanism 110 transports the tampon 10 in such a manner that the rear end of the applicator 30 passes through both of the pair of cut-away portions 141a (i.e., in such a manner that the rear end part of the applicator 30 passes inside the leading end part of the suction pipe 141), In other words, the positional relationship in the intersecting direction between the transport path of the tampon 10 and the suction pipe 141 is, as shown in FIG. 10, such that the rear end part of the applicator 30 of the tampon 10 and the leading end part of the suction pipe 141 overlap when the tampon 10 comes to a position, in the transport direction, where the suction pipe 141 is situated. Here, since the cut-away portions 141a are formed at the leading end part of the suction pipe 141, the rear end part of the applicator 30 is capable of entering inside the leading end part of the suction pipe 141 through the cut-away portion 141a on the upstream side in the transport direction and leave from the leading end part through the cut-away portion 141a on the downstream side in the transport direction.

The pull-out mechanism 140 of the above-described structure sucks the air inside the suction pipe 141 by the pre-suction operation, during the transport of the tampon 10 while the rear end of the applicator 30 is situated between the pair of cut-away portions 141a in the transport direction (i.e., when the rear end part of the applicator 30 is situated inside the leading end part of the suction pipe 141). Thus, in a case where the portion of the cord 22 that, is supposed to be the exposing portion 22a is not properly exposed from the rear end of the applicator 30, the cord 22 (specifically, the portion that is supposed, to be the exposing portion 22a) will be pulled out. Also, during the pre-suction operation, since the rear end part of the applicator 30 is situated inside the leading end part of the suction pipe 141, the cord 22 can be pulled out. efficiently.

The pull-cut mechanism 140 of the present embodiment uses a suction pump 132 of the suction mechanism 130 as the suction source. In other words, in the present embodiment, the suction mechanism 130 and the pull-out mechanism 140 share the suction source. On the other hand, when pulling out the cord 22 from the rear end of the applicator 30 with the pre-suction operation, a suction force needs to be greater than the suction force for extending the cord 22 along the longitudinal direction of the tampon 10 with the suction operation. Therefore, in the present embodiment, the leading end side opening of the suction pipe 141 (i.e., an air inlet during the pre-suction operation) is narrower than the opening 127 of the casing 122 (i.e., an air inlet during the suction operation). (See FIGS. 12C and 13). As a result, even the suction mechanism 130 and the pull-out mechanism 140 share a Single suction source (i.e., the suction pump 132), a suction force required for pulling out the cord 22 in the pre-suction operation is appropriately ensured.

Note that the suction source is not limited to a structure in which it is shared between the suction mechanism 130 and the pull-out mechanism 140, and each of the suction mechanism 130 and the pull-out mechanism 140 may include an individual suction source.

Figure 14:
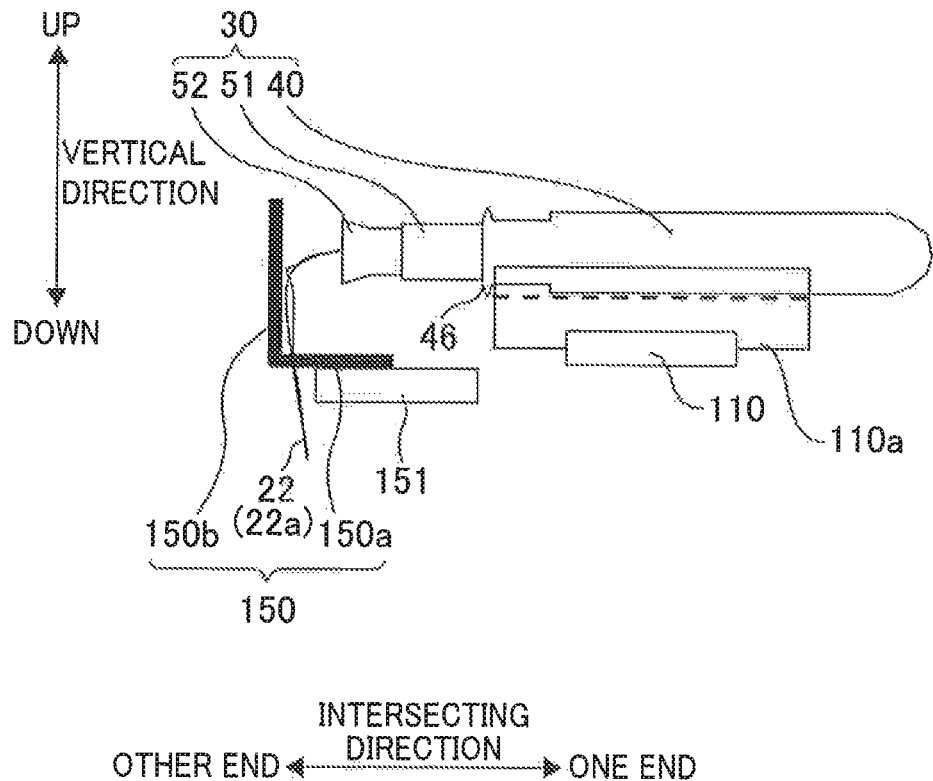
FIG. 14 is a diagram showing a contacting member 150.

The contacting member 150 is a rod provided upstream of the pull-out mechanism 140 in the transport direction. As shown in FIG. 14, when the contacting member 150 is viewed from the upstream side in the transport direction, the contacting member 150 is bent in an L-shape and has an intersecting part 150a extending in the intersecting direction and a vertical part 150b extending in the vertical direction. FIG. 14 is a diagram showing the contacting member 150 in which the contacting member 150 is viewed from the upstream side in the transport direction.

As shown in FIG. 14, the contacting member 150 is supported by a substantially rectangular bracket 151 in such a manner that the intersecting part 150a of the contacting member 150 is fixed to the bracket 151. Further, the contacting member 150 is arranged in such a manner that the intersecting part 150a and the vertical part 150b are in contact with the cord 22 (specifically, the exposing portion 22a of the cord 22) of the tampon 10 that is being transported. Note that the positional relationship between the tampon 10 that is being transported and the contacting member 150 is as shown in FIGS. 10 and 14.

Then, the contacting member 150 comes into contact with the exposing portion 22a of the cord 22 of the tampon 10 while the tampon 10 is being transported. As a result, the exposing portion 22a will be caught by the contacting member 150. That is to say, the tampon 10 is transported in the transport direction in such a manner that the exposing portion 22a comes into contact with the contacting member 150 and is caught by the contacting member 150. Thus, the contacting member 150 prevents the exposing portion 22a from being sucked towards the suction pipe 141 by catching the exposing portion 22a of the cord 22 with the contacting member 150.

Explaining in detail, when one of the tampons 10 arrives at a position along the transport direction at which the suction pipe 141 is situated and while the pre-suction operation is being performed on the one of the tampons 10, the contacting member 150 comes into contact with an exposing portion 22a of a cord 22 of another one of the tampons 10 that is upstream of and adjacent to the one of the tampons 10 in the transport direction. Thus, the exposing portion 22a of the cord 22 of the other one of the tampons 10 is prevented from being sucked towards the suction pipe 141. As a result, the cord 22 of the tampon 10 that is under the pre-suction operation and. the cord 22 of the tampon 10 that is downstream of and adjacent to such tampon 10 can be prevented from being tangled to each other.

<<Example of Operation of Inspecting Apparatus 100>>

Next, the inspecting step by the inspecting apparatus 100 will be described as an example of operation of the inspecting apparatus 100 of the above-described structure.

The inspecting step by the inspecting apparatus 100 starts with supplying each of the tampons 10 manufactured in a main manufacturing step S002 to the inspecting apparatus 100. After being supplied to the inspecting apparatus 100, first, each of the tampons 10 is set on the holder 110a by a setting mechanism (not shown). Here, each of the tampons 10 is set with a posture in which its longitudinal direction is lying along the intersecting direction (a transversely-situated posture). Then, the tampon 10 that is set on the holder 110a is transported in the transport direction by the transport mechanism 110 while maintaining the above-mentioned posture (see FIG. 10). Note that the tampon 10 is transported with a portion of the cord 22 being somewhat exposed from the rear end of the applicator 30.

Also, the transport mechanism 110 sequentially transports each of the tampons 10 in such a manner that each of the tampons 10 is arranged at a constant, interval along the transport direction. Note that each of the tampons 10 arranged in the transport direction is transported in such a manner that the leading end positions of the tampons 10 are aligned with each other.

Viewing from the tampon 10 that is being transported, the casing 122, the suction pipe 141 and the contacting member 150 are each situated on the other-end side in the intersecting direction. That is, the transport mechanism 110 transports each of the tampons 10 in such a manner that each of the tampons 10 is situated on the opening 127 side of the casing 122 in the intersecting direction, with, the longitudinal direction of each of the tampons 10 being lying along the intersecting direction.

As the transport mechanism 110 transports the tampon 10 to the downstream side in the transport direction, the tampon 10 passes by a position at which the exposing portion 22a of the cord 22 comes into contact with the contacting member 150, and then arrives at a position at which the rear end of the applicator 30 reaches the leading end part of the suction pipe 141. Thereafter, the transport mechanism 110 transports the tampon 10 in such a manner that the rear end of the applicator 30 passes through, both of the pair of cut-away portions 141a formed at the leading-end part of the suction pipe 141. Then, when the rear end of the applicator 30 is at a position between the cut-away portions 141a in the transport direction, the pull-out mechanism 140 performs an operation of sucking air inside the suction pipe 141 (i.e., pre-suction operation), Thus, in a case where a portion of the cord 22 that is supposed to be the exposing portion 22a. is remaining inside the applicator 30, the cord 22 (specifically, a portion of the cord 22 that is supposed to be the exposing portion 22a) will be pulled out from the rear end of the applicator 30, It is to be noted that, while the pre-suction operation is performed on one of the tampons 10, the tampon 10 that is upstream of and adjacent to such tampon 10 in the transport direction is in a state where the exposing portion 22a of the cord 22 is in contact with, the contacting member 150 and is caught by the contacting member 150. As a result, as has been described above, the cords 22 (specifically, the exposing portions 22a) are prevented from tangling with each other between the tampon 10 that, is under pre-suction operation and the tampon 10 that is upstream of and adjacent to such tampon 10 in the transport, direction.

Then, the tampon 10 is further transported to the downstream side in the transport direction and the rear end of the applicator 30 of such tampon 10 passes through the cut-away portion 141a on the downstream side in the transport direction and leaves the leading end part of the suction pipe 141. At this time, the exposing portion 22a of the cord 22 is, from the one end or the exposing portion 22a (an end situated at the rear end of the applicator 30) to the other end thereof (the rear end of the cord 22), rubbed against an edge of the cut-away portion 141a on the downstream side in the transport direction. Thus, in a case where there is a twist produced in the cord 22, the twist will be eliminated.

Thereafter, the transport mechanism 110 transports the tampon 10 further to the downstream side in the transport direction. Then, when the tampon 10 arrives at a position in the transport direction where the cord-length inspecting mechanism 120 is provided, the cord-length inspecting mechanism 120 performs an operation of inspecting the length of the cord 22 of the tampon 10 (hereinafter referred, to as the inspecting operation). Hereinafter, the flow of the inspecting operation performed by the cord-length inspecting mechanism 120 will be described.

After being transported to a position, before the position at which the casing 122 is provided in the transport direction, the tampon 10 moves to the downstream side in the transport direction in such a manner that the exposing portion 22a of the cord 22 enters the gap 126, formed between the lower wail 123 and the upper wall 124. It is to be noted that because both ends in the transport direction of the gap 126 are open ends, the exposing portion 22a will enter into the gap 126 from the upstream side end in the transport direction of the gap 126. Further, as has been described above, the spacing of the gap 126 is somewhat greater than the spacing at the central part in the transport direction at both end sides in the transport direction, Therefore, the exposing portion 22a can easily enter into the gap 126. Also, when the exposing portion 22a enters inside the gap 126, the rear end of the cord 22 is rubbed against one-end surface in the intersecting direction of the end part 123c of the side wall 125 (see FIG. 10).

Thereafter, the tampon 10 moves to the downstream, side in the transport direction in such a manner that the exposing portion 22a passes through the gap 126. That is, the transport mechanism 110 transports the tampon 10 in such si manner that the exposing portion 22a passes through the gap 126. At this time, the rear end of the applicator 30 is situated outside (on the one-end side in the intersecting direction) of the opening 127 of the casing 122, The positional relationship between the tampon 10 that is being transported and the casing 122 is such a relationship that the leading-end-side end surface of the annular rib 46 of the outer cylinder 40 of the tampon 10 (i.e., the above-described reference position) is situated, on the one-end side in. the intersecting direction by a predetermined distance (in the present embodiment, approximately 44 mm) from the one ends in the intersecting direction of the lower wall 123 and the upper wall 124.

Then, while the exposing portion 22a is passing through the gap 126, the tampon 10 comes to a position at which the length of the cord 22 of the tampon 10 is inspected by the sensors 121. When the tampon 10 is situated at such position, the cord-length inspecting mechanism 120 inspects the length of the cord 22 based on signals outputted by the sensors 121, respectively, in accordance with the detection result.

On the other hand, as has been described above, during the transport period of the tampon 10, the suction pump 132 provided in the suction mechanism 130 is continuously in operation. Therefore, the suction mechanism 130 continuously sucks the air inside the casing 122 even, when the exposing portion 22a of the cord 22 is traveling in the gap 126. Here, the suction mechanism 130 sucks the air inside the casing 122 via the hole 123a formed in the lower wall 123 of the casing 122, Also, the hole 123a is formed sit the central, part in the transport direction of the lower-wall 123, Further, the hole 123a is situated on the other-end side in the intersecting direction of the lower wall 123 (specifically, on the other-end. side in the intersecting direction of the other-end side sensor 121c in the intersecting direction).

Figure 15:
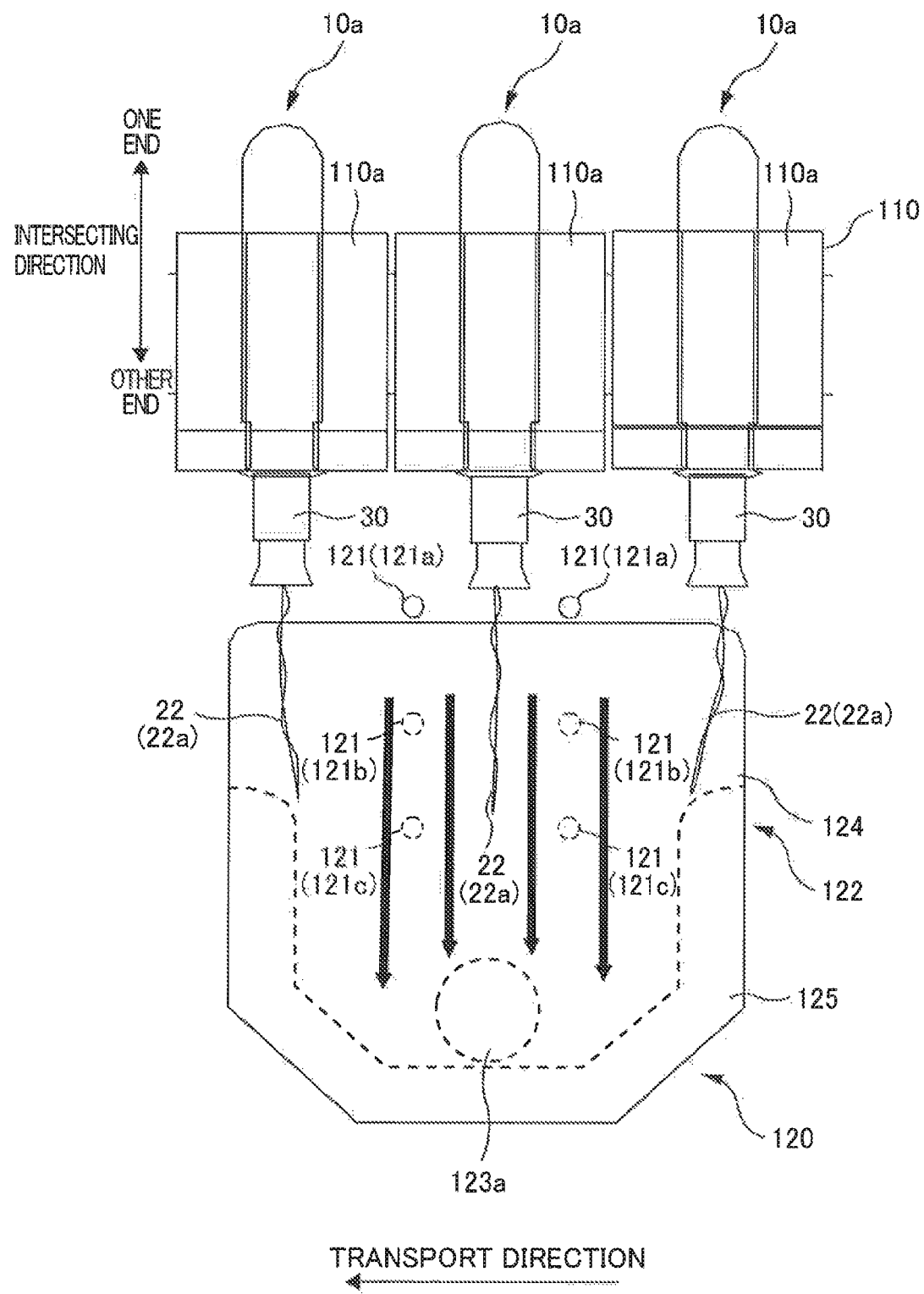
FIG. 15 is a diagram showing inside of the casing 122 during inspecting operation of a cord-length inspecting mechanism 120.

As a result, as shown in FIG. 15, when the suction mechanism 130 performs a suction operation, an airflow (shown by thick arrows in FIG. 15) is generated that flows in the gap 126 from one-end side to the other-end side in the intersecting direction towards the above-described hole 123a. FIG. 15 is a diagram showing an inside of the casing 122 during the inspecting operation of the cord-length inspecting mechanism 120, Further, near the central part in the transport direction of the gap 126, the above-mentioned airflow is regulated to flow substantially parallel to the intersecting direction. This is because the hole 123a which is an air cutler of the above-mentioned airflow is situated at a positron corresponding to the central part in one transport direction of the gap 126 and the suction pressure of the suction pump 132 is regulated in such a manner that the suction mechanism 130 sucks the air inside the casing 122 at an appropriate suction force.

In the present embodiment, the sensors 121 are provided, within a range in which the airflow is regulated in a manner described above in the transport direction. Therefore, when, the exposing portion 22a of the cord 22 of the tampon 10 passes through the central part in the transport direction of the gap 126 (i.e., at a position where the length of the cord 22 is inspected by the sensors 121 in the transport direction), the cord 22 is extended substantially straight by being blown by the regulated airflow. That is to say, when the cord-length inspecting mechanism 120 inspects the length of the cord 22, the cord 22 is extended along the longitudinal direction of the tampon 10 by the suction operation.

In the present embodiment, the suction mechanism 130 sucks air at the other-end side in the intersecting direction, of the tampon 10 that is being transported (on the other-end side in the intersecting direction of the rear end of the cord 22 of the tampon 10) to thereby extend the cord 22 of the tampon 10 along the longitudinal direction of the tampon 10. To be more specific, the suction mechanism 130 sucks air inside the casing 122 while the exposing portion 22a of the cord 22 is passing through the gap 126 to thereby extend, the cord 22 along the longitudinal direction of the tampon 10. Then, while the suction mechanism 130 is sucking the air in a manner described above, the cord-length inspecting mechanism 120 performs an inspecting operation of inspecting the length of the cord 22. As a result, the length of the cord 22 of the tampon 10 will be inspected in a state where the cord 22 is extended straight along the longitudinal direction of the tampon 10.

Also, in. the present embodiment, the cord-length inspecting mechanism 120 inspects the length of the cord 22 using the above-described three sensors 121 (that is, one-end side sensor 121a, middle sensor 121b and other end side sensor 121c . That is to say, the cord-length inspecting mechanism 120 inspects the length of the cord 22 based on output signals from the respective three sensors 121, when the tampon 10 passes by the positions at which the three sensors 121 are provided in the transport direction (i.e., the positions at which the length of the cord 22 is inspected by the sensors 121). Hereinafter, a detailed explanation is made on how the cord-length inspecting mechanism 120 inspects the length of the cord 22 in the inspecting operation. In the following, among the signals outputted by each of the sensors 121, the signal outputted when the exposing portion 22a of the cord 22 has passed the position at which each of the sensors 121 is provided is referred to as a cord presence signal and the signal outputted when the exposing portion 22a has not passed the above-mentioned position is referred to as a cord absence signal.

In a state where the cord 22 of the tampon 10 is extended along the longitudinal direction of the tampon 10, when the rear end of the cord 22 has passed between the middle sensor 121b and the other-end side sensor 121c, the one-end side sensor 121a and the middle sensor 121b outputs the cord presence signal and the other-end side sensor 121c outputs the cord absence signal. In such a case, the cord-length inspecting mechanism 120 determines that the length of the cord 22 is normal.

On the other hand, in a case where the rear end of the cord 22 has passed between the one-end side sensor 121a and the middle sensor 121b in the intersecting direction, only the one-end. side sensor 121a outputs the cord presence signal and the cord-length inspecting mechanism 120 determines that the length of the cord 22 is shorter than normal (not normal) . Also, when the rear end of the cord 22 has passed the position on. the other-end side than the other-end side sensor 121c in the intersecting direction, ail of the three sensors 121 output the cord presence signals and the cord-length inspecting mechanism 120 determines that the length of the cord 22 is longer than normal (not normal). Further, in a case where the rear end of the cord 22 passes a position on the one-end side than the one-end side sensor 121a in the intersecting direction, and in a case where the cord 22 is detached from the tampon main body 20 (or the cord 22 is not sewn on the cotton body 21 to start with), all of the three sensors 121 output the cord absence signals and the cord-length inspecting mechanism 120 determines that the length of the cord 22 is not normal.

As has been described above, in the present embodiment, in order to improve an inspecting accuracy, two sets of three sensors 121 are provided. In other words, in the present embodiment, while the exposing portion 22a of the cord 22 of the tampon 10 is passing through the gap 126, the cord-length inspecting mechanism 120 performs the inspection of the length of the cord 22 twice, here, the two sets of three sensors 121 sire both provided within a range that the above-mentioned airflow is regulated in the transport direction. Therefore, the two inspections performed by the cord-length inspecting mechanism 120 are both performed in a state where the cord 22 is extended along the longitudinal direction of the tampon 10.

Thereafter, as the transport mechanism 110 transports the tampon 10 to the downstream side in the transport direction, the exposing portion 22a of the cord 22 of the tampon 10 leaves the gap 126 from the downstream, side end in the transport direction of the gap 126. After the above-mentioned series of operations, the inspecting operation by the cord-length inspecting mechanism 120 is terminated (i.e., the inspecting operation by the inspecting apparatus 100 is completed). Then, the tampon 10 that has been determined that the length of the cord 22 is normal in the above-mentioned inspection operation (specifically, the tampon 10 that has been determined that the length of the cord 22 is normal at each of the two inspection) is continuously transported, to the next wrapping step. On the other hand, the tampon 10 that has been determined in the above-mentioned inspecting operation that, the length of the cord 22 is not normal (specifically, the tampon 10 that has been determined that the length of the cord 22 is not normal in at least one of the two inspection) is collected as a defective product by a collecting mechanism (not shown).

— Effectiveness of Inspecting Apparatus 100 of the Present Embodiment —

As has been described above, in. the inspecting apparatus 100 of the tampon 10 of the present embodiment, the suction mechanism 130 performs a suction operation and extends the cord 22 of the tampon 10 along the longitudinal direction of the tampon 10, and the cord-length inspecting mechanisms 120 inspects the length of the cord 22 during the above-mentioned suction operation. In other words, the inspecting method of the tampon 10 of the present embodiment includes the step of extending the cord 22 along the longitudinal direction of the tampon by sucking air by the suction mechanism 130 (specifically, the above-mentioned suction operation) and the step of inspecting the length of the cord 22 while the suction mechanism 130 is sucking the air (specifically, the inspection operation by the inspecting mechanism 120), Thus, according to the present embodiment, the length of the cord 22 can be accurately inspected.

That is, as has been described above: in the summary, even if the length of the cord 22 is inspected in a state where the cord 22 is flopping (or the cord 22 is swinging) or the cord 22 is slack, it is difficult to obtain an accurate inspection result.

On the contrary, in accordance with the inspecting apparatus 100 of the present embodiment, the length of the cord 22 can be inspected, while keeping the cord 22 in a state where it is extended along the longitudinal direction of the tampon 10 (or simply stating, in a state where it is extended straight). As a result, the length of the core 22 can be inspected accurately.

The cord-length inspecting mechanism 120 of the present embodiment has the casing 122 that includes the lower wall 123 and the upper wall 124 (corresponding to the pair of walls) that lie along the transport direction. While the exposing portion 22a of the cord 22 is passing through the gap 126 between the lower wall 123 and the upper wall 124, the suction mechanism 130 sucks the air inside the casing 122 at the other-end side in the intersecting direction than the rear end of the cord 22. Thus, the cord 22 is extended along the longitudinal direction of the tampon 10. Meanwhile, the cord-length inspecting mechanism 120 inspects the length of the cord 22 by the sensors 121. The above-mentioned structure is a simple structure for inspecting the length of the cord 22 while extending the cord 22 straight. That is, in the present embodiment, the length of the cord 22 can be inspected accurately with a simple structure.

In other words, another structure for inspecting the length of the cord 22 while extending the cord 22 straight may include a suction apparatus at the rear end side of the tampon 10 that is being transported and the suction apparatus may be moved in the transport direction together with the tampon 10. With such a structure, during the transport period of the tampon 10, the cord 22 can be extended straight along the longitudinal direction of the tampon 10. Therefore, by inspecting the length of the cord 22 while the tampon 10 that is being transported, the length of the cord 22 can be inspected while keeping the cord 22 straight. However, with such a structure, it is necessary to separately provide a driving mechanism that is adapted to move the suction apparatus. On the contrary, according to the present embodiment, the length of the cord 22 can be inspected while keeping the cord 22 straight using a stationary suction mechanism 130.

Also, according to the present embodiment, the lower wall 123 has the hole 123a that is formed at the central part in the transport direction thereof and the suction mechanism 130 sacks the air inside the casing 122 through the hole 123a. Further, the hole 123a is situated at the other-end side in the intersecting direction than, the sensors 121 (specifically, the other end side sensor 121c). With the structure described above, the inspection of the length of the cord 22 can be performed properly on each of the tampons 10 that is sequentially sent to the cord-length inspecting mechanism 120.

To be more specific, according to the above-mentioned structure, when the suction operation is performed by the suction mechanism 130, the airflow that is regulated to flow along the intersecting direction is generated at the central part in the transport direction of the gap 126 between the lower wall 123 and the upper wall 124, With such airflow, the cord 22 is extended straight when the exposing portion 22a of the cord 22 passes through the central part in the transport direction of the gap 126. Further, a position at which the length of the cord 22 is inspected by the middle sensor 121b (which corresponds to the first optical sensor 121) and the other end side sensor 121c (which corresponds to the second optical sensor) is situated within a range that the airflow is regulated (i.e., the central part in the transport direction of the gap 126). Then, when the exposing portion 22a of the cord 22 of the tampon 10 passes through the central part in the transport direction of the gap 126, cord-length inspecting mechanism 120 inspects the length of the cord 22 by the middle sensor 121b and the other end side sensor 121c. As a result, it is positively ensured that the length of the cord 22 is inspected while the cord 22 is extended straight.

Also, in the present embodiment, the three sensors 121 provided in the cord-length inspecting mechanism 120 (i.e., the one-end side sensor 121a, the middle sensor 121b and the other end side sensor 121c) are situated at mutually different positions in the intersecting direction. In a case where the length of the cord 22 is normal when extended, along the longitudinal direction of the tampon 10, the rear end of the cord 22 passes between the middle sensor 121b and one other end side sensor 121c in the intersecting direction. Thus, it is possible to properly inspect whether the length of the cord 22 is normal (specifically, a length within a standard range).

Also, in the present embodiment, the pull-out mechanism 140 is provided upstream of the cord-length inspecting mechanism 120 in the transport direction. Each of the tampons 10 is subject to the pre-suction operation by the pull-out mechanism 140 before being subject to the suction operation by the suction mechanism 130 (before the cord 22 is extended along the longitudinal direction of the tampon 10). Then, with such pre-suction operation, the cord 22 that has not been properly exposed from the rear end of the applicator 30 (specifically, the portion that is supposed to be the exposing portion 22a) is pulled out from the rear end. As a result, it is possible to prevent the cord-length inspecting mechanism 120 from falsely determining that the length of the cord 22 is not normal in a case where, even though the length of the cord 22 is normal, its exposing portion 22a is not properly exposed from the rear end of the applicator 30.

Further, according to the present embodiment, the pair of cut-away portions 141a sire formed at the leading end part of the suction pipe 141 of the pull-out mechanism 140. The transport mechanism 110 transports the tampon 10 in such a manner that the rear end part of the applicator 30 enters inside the leading end part of the suction pipe 141 through the cut-away port ions 141a. Then, the pre-suction operation is performed when the rear end part of the applicator 30 is situated reside the leading-end part of the suction pipe 141. Accordingly, the cord 22 that is not properly exposed from the rear end of the applicator 30 can be pulled out efficiently.

— Other Embodiments —

The inspecting apparatus 100 and inspecting method for inspecting the tampon 10 of the present invention have been described with reference to the above embodiment. However, the above-described embodiment is provided for the purpose of facilitating the understanding of the present invention only and does not give any limitation to the present invention. It goes without saying that any modifications and improvements to the present invention can be made without departing from the spirit of the invention and the present invention includes its equivalents. Further, the above-mentioned setting values, sizes, and configurations, etc., are merely examples to produce the effect of the present invention and should not be understood as any limitation to the present invention.

The above-described embodiment is directed to the tampon 10 having the inner cylinder 50 of a two-tier telescopic type. However, the present invention is not limited to such a structure. For example, the tampon 10 may be of a type that, includes the inner cylinder 50 with a fixed length (not telescopic).

Also, in the above embodiment, each of the tampons 10 is transported by the transport mechanism 110 while maintaining the transversely-placed posture. However, the present invention is not limited to such posture and each of the tampons 10 may be transported in the transport direction while maintaining a posture in which its longitudinal direction lies along the vertical direction (longitudinally-placed posture).

That is to say, in FIG. 10, the intersecting direction may correspond, to the vertical direction. Even in, such a case, the length of the cord 22 can be accurately inspected by performing the suction operation by the suction mechanism 130 on each of the tampons 10 while transporting each of the tampons 10 and inspecting the length, of the cord 22 of each of the tampons 10 during such suction operation.

List of Reference Numerals 10 tampon, 20 tampon main body, 21 cotton body, 22 cord, 22a exposing portion,
23 cotton strip, 30 applicator, 40 outer cylinder, 41 major diameter part, 42 minor diameter part, 43 leading-end opening, 44 petaloid part, 45 rear-end opening,
46 annular rib, 47 stepped part, 50 inner cylinder, 51 first inner cylinder,
51a flange part, 51b annular protrusion, 52 second inner cylinder, 52a flange part,
52b protruded part, 52c flared part,
100 inspecting apparatus, 110 transport mechanism, 110a holder,
120 cord-length inspecting mechanism,
121 sensor, 121a first-end sensor, 121b middle sensor (first optical sensor),
121c other-end sensor (second optical sensor), 122 casing, 123 lower wall (wall), 123a hole, 124 upper wall (wall), 125 side wall (other wall),
125a central part, 125b inclined part, 125c end part, 126 gap, 127 opening,
130 suction mechanism, 131 duct, 132 suction pump, 140 pull-out mechanism,
141 suction pipe, 141a cut-away portion, 142 connection pipe, 150 contacting member,
150a intersecting part, 150b vertical part, 151 bracket, 200 pressing machine

What is claimed is:

1. An inspecting apparatus for inspecting a tampon, the tampon including a tampon main body that has a cord and an applicator that accommodates the tampon main body, wherein the cord has an exposing portion exposed from a rear end of the applicator, the inspecting apparatus comprising:
a suction mechanism configured to extend the cord along a longitudinal direction of the tampon by sucking air;
a cord-length inspecting mechanism configured to inspect a length of the cord while the suction mechanism is sucking the air; and
a transport mechanism configured to transport the tampon in a transport direction intersecting the longitudinal direction of the tampon,
wherein
the cord-length inspecting mechanism includes:
a casing having opposing first and second walls lying along the transport direction; and
a sensor configured to inspect the length of the cord and provided in a gap between the first and second walls,
the transport mechanism is configured to transport the tampon in such a manner that the exposing portion of the cord passes through the gap along the transport direction,
the cord-length inspecting mechanism is configured to inspect the length of the cord by the sensor while the suction mechanism is sucking the air,
the casing of the cord-length inspecting mechanism further includes:
an opening defined by the gap and formed at a first side of the casing in an intersecting direction, said intersecting direction intersecting the transport direction;
a third wall closing the gap at a second side opposite to the first side in the intersecting direction; and
a hole formed in either the first wall, the second wall, or the third wall,
the transport mechanism is configured to transport the tampon in the transport direction with the longitudinal direction of the tampon lying along the intersecting direction and the tampon being situated in the opening in the intersecting direction,
the sensor is configured to inspect the length of the cord at a central part of the gap in the transport direction,
the hole is situated on the second side of the casing, and
the suction mechanism is configured to suck the air inside the casing through the hole.

2. An inspecting apparatus for inspecting a tampon, the tampon including a tampon main body that has a cord and an applicator that accommodates the tampon main body, wherein the cord has an exposing portion exposed from a rear end of the applicator, the inspecting apparatus comprising:
a suction mechanism configured to extend the cord along a longitudinal direction of the tampon by sucking air;
a cord-length inspecting mechanism configured to inspect a length of the cord while the suction mechanism is sucking the air; and
a transport mechanism configured to transport the tampon in a transport direction intersecting the longitudinal direction of the tampon,
wherein the cord-length inspecting mechanism includes a first optical sensor and a second optical sensor,
wherein the first optical sensor and the second optical sensor are situated at mutually different positions in an intersecting direction intersecting the transport direction, and
wherein the transport mechanism is configured to transport the tampon in such a manner that, in a case where the length of the cord extended along the longitudinal direction of the tampon is normal, the exposing portion of the cord passes between the first optical sensor and the second optical sensor in the intersecting direction.

3. The inspecting apparatus as claimed in claim 1, further comprising:
a pull-out mechanism configured to pull out a portion that is to be the exposing portion of the cord from the rear end of the applicator,
wherein the pull-out mechanism is provided upstream of the cord-length inspecting mechanism in the transport direction and configured to pull out the portion that is to be the exposing portion by sucking the air.

4. The inspecting apparatus as claimed in claim 3,
wherein the pull-out mechanism includes a suction pipe that extends along the intersecting direction,
wherein the suction pipe has a leading end part and a pair of cut-away portions opposing each other in the transport direction at the leading end part of the suction pipe,
wherein the transport mechanism is configured to transport the tampon in such a manner that the rear end of the applicator passes through both of the pair of cut-away portions, and
wherein the pull-out mechanism is configured to pull out the portion that is to be the exposing portion by sucking the air inside the suction pipe when the rear end of the applicator is situated between the cut-away portions in the transport direction.

5. The inspecting apparatus as claimed in claim 3, further comprising:
a contacting member configured to contact the exposing portion, wherein the contacting member is provided upstream of the pull-out mechanism in the transport direction, and wherein the contacting member is configured to catch and contact the exposing portion when said transport mechanism transports the tampon.

6. An inspecting method of inspecting a tampon, the tampon including a tampon main body having a cord, and an applicator for accommodating the tampon main body, wherein the cord has an exposing portion exposed from a rear end of the applicator, the inspecting method comprising:

extending the cord along a longitudinal direction of the tampon by sucking air by a suction mechanism; and inspecting a length of the cord with a cord-length inspecting mechanism while the suction mechanism is sucking the air; and transporting the tampon with a transport mechanism in a transport direction intersecting the longitudinal direction of the tampon, wherein the cord-length inspecting mechanism includes:
- a casing having opposing first and second walls lying along the transport direction; and
- a sensor inspecting the length of the cord and provided in a gap between the first and second walls, said transporting is performed so that the exposing portion of the cord passes through the gap along the transport direction, said inspecting is performed by the sensor while the suction mechanism is sucking the air, the casing of the cord-length inspecting mechanism further includes:
- an opening defined by the gap and formed at a first side of the casing in an intersecting direction, said intersecting direction intersecting the transport direction;
- a third wall closing the gap at a second side opposite to the first side in the intersecting direction; and
- a hole formed in either the first wall, the second wall, or the third wall, said transporting the tampon in the transport direction is performed so that the tampon is situated in the opening in the intersecting direction, said inspecting is performed at a central part of the gap in the transport direction, the hole is situated on the second side of the casing, and said extending is performed by sucking the air inside the casing through the hole.

* * * * *